(12) United States Patent
Chen et al.

(10) Patent No.: US 9,778,188 B2
(45) Date of Patent: Oct. 3, 2017

(54) APPARATUS AND METHOD FOR DETECTION AND DISCRIMINATION MOLECULAR OBJECT

(75) Inventors: Hung-Chun Chen, Hsinchu (TW); Ming-Chia Li, Dajia Township, Taichung County (TW); Chang-Sheng Chu, Hsinchu (TW); Yu-Tang Li, Tucheng (TW); Chung-Fan Chiou, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 417 days.

(21) Appl. No.: 12/720,352

(22) Filed: Mar. 9, 2010

(65) Prior Publication Data

US 2010/0256918 A1 Oct. 7, 2010

Related U.S. Application Data

(60) Provisional application No. 61/159,310, filed on Mar. 11, 2009.

(51) Int. Cl.
| | | |
|---|---|---|
| *G01N 33/48* | (2006.01) | |
| *G01N 21/64* | (2006.01) | |
| *C12Q 1/68* | (2006.01) | |
| *G01N 15/14* | (2006.01) | |

(52) U.S. Cl.
CPC ....... *G01N 21/6428* (2013.01); *C12Q 1/6869* (2013.01); *G01N 21/645* (2013.01); *G01N 15/1459* (2013.01); *G01N 2015/149* (2013.01); *G01N 2015/1477* (2013.01); *G01N 2021/6441* (2013.01)

(58) Field of Classification Search
None
See application file for complete search history.

(56) References Cited

U.S. PATENT DOCUMENTS

| | | |
|---|---|---|
| 4,748,111 A | 5/1988 | Dattagupta et al. |
| 4,790,614 A | 12/1988 | Imoto et al. |
| 5,034,613 A | 7/1991 | Denk et al. |
| 5,162,887 A | 11/1992 | Dierschke |
| 5,185,832 A | 2/1993 | Coutandin et al. |
| 5,302,509 A | 4/1994 | Cheeseman |
| 5,355,022 A * | 10/1994 | Sugahara ............ H01L 21/2007 257/506 |
| 5,391,480 A | 2/1995 | Davis et al. |
| 5,405,747 A | 4/1995 | Jett et al. |
| 5,460,975 A | 10/1995 | Freitag et al. |
| 5,674,743 A | 10/1997 | Ulmer |
| 5,717,602 A | 2/1998 | Kenning |
| 5,750,341 A | 5/1998 | Macevicz |
| 5,795,782 A | 8/1998 | Church et al. |
| 5,965,875 A | 10/1999 | Merrill |
| 6,013,434 A | 1/2000 | Tregear et al. |
| 6,091,874 A | 7/2000 | Higashi et al. |
| 6,123,819 A | 9/2000 | Peeters |
| 6,153,737 A | 11/2000 | Manoharan et al. |
| 6,197,513 B1 | 3/2001 | Coull et al. |
| 6,210,973 B1 | 4/2001 | Pettit |
| 6,232,075 B1 | 5/2001 | Williams |
| 6,255,083 B1 | 7/2001 | Williams |
| 6,306,607 B2 | 10/2001 | Williams |
| 6,344,653 B1 | 2/2002 | Webb et al. |
| 6,362,002 B1 | 3/2002 | Denison et al. |
| 6,374,019 B1 | 4/2002 | Gustavsson |
| 6,413,792 B1 | 7/2002 | Sauer et al. |
| 6,618,536 B1 | 9/2003 | Heideman et al. |
| 6,762,048 B2 | 7/2004 | Williams |
| 6,917,726 B2 | 7/2005 | Levene et al. |
| 6,946,249 B2 | 9/2005 | Head et al. |
| 7,013,054 B2 | 3/2006 | Levene et al. |
| 7,015,485 B2 | 3/2006 | Kitagawa |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,060,440 B1 | 6/2006 | Kless |
| 7,081,526 B2 | 7/2006 | Marciacq et al. |
| 7,167,735 B2 | 1/2007 | Uchida et al. |
| 7,170,050 B2 | 1/2007 | Turner et al. |
| 7,175,811 B2 | 2/2007 | Bach et al. |

(Continued)

FOREIGN PATENT DOCUMENTS

| | | |
|---|---|---|
| CN | 1545619 A | 11/2004 |
| CN | 1576844 A | 2/2005 |
| CN | 1708680 A | 12/2005 |
| CN | 101168773 A | 4/2008 |
| CN | 101384729 A | 3/2009 |
| CN | 101654712 A | 2/2010 |
| CN | 101711257 A | 5/2010 |
| CN | 101726462 A | 6/2010 |
| EP | 1309719 | 2/2002 |
| EP | 1089067 B1 | 12/2004 |

(Continued)

OTHER PUBLICATIONS

Extended European search report, issued by the European Patent office, dated Aug. 12, 2011, in European patent application No. 10750363.3 (17 pages).

Extended European search report, issued by the European Patent office, dated Aug. 16, 2011, in European patent application No. 10196884.0 (10 pages).

C. Adessi et al., "Solid phase DNA amplification: characterization of primer attachment and amplication mechanisms," Nucleic Acids Research, vol. 28, No. 20, e87 (2000).

(Continued)

*Primary Examiner* — Anna Skibinsky
(74) *Attorney, Agent, or Firm* — Finnegan, Henderson, Farabow, Garrett & Dunner LLP

(57) ABSTRACT

An apparatus for detecting an object capable of emitting light. The apparatus comprises a light detector comprising at least two optical sensors capable of determining the intensity of the light; and a computer processing output signal generated by the optical sensors and comparing a result of the processing with a known result corresponding to a known type to determine whether the object belongs to the known type.

27 Claims, 14 Drawing Sheets

(56) References Cited

U.S. PATENT DOCUMENTS

| | | |
|---|---|---|
| 7,181,122 B1 | 2/2007 | Levene et al. |
| 7,226,777 B2 | 6/2007 | Kawamura et al. |
| 7,229,799 B2 | 6/2007 | Williams |
| 7,282,337 B1 | 10/2007 | Harris |
| 7,292,742 B2 | 11/2007 | Levene et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,316,930 B1 | 1/2008 | Montalbo |
| 7,329,492 B2 | 2/2008 | Hardin et al. |
| 7,361,466 B2 | 4/2008 | Korlach et al. |
| 7,384,797 B1 | 6/2008 | Blair |
| 7,416,844 B2 | 8/2008 | Korlach et al. |
| 7,485,424 B2 | 2/2009 | Korlach et al. |
| 7,486,865 B2 | 2/2009 | Foquet et al. |
| 7,666,645 B2 | 2/2010 | Wang |
| 7,767,441 B2 | 8/2010 | Chiou et al. |
| 7,805,081 B2 | 9/2010 | Lundquist et al. |
| 7,943,305 B2 | 5/2011 | Korlach et al. |
| 7,943,307 B2 | 5/2011 | Korlach et al. |
| 8,252,581 B2 | 8/2012 | Joseph et al. |
| 8,603,741 B2 | 12/2013 | Emig et al. |
| 2002/0090630 A1 | 7/2002 | Hazama |
| 2002/0110839 A1 | 8/2002 | Bach et al. |
| 2002/0141062 A1* | 10/2002 | Christoffersen ..... G02B 5/1852 |
| | | 359/566 |
| 2002/0154315 A1* | 10/2002 | Myrick .......................... 356/451 |
| 2003/0064366 A1 | 4/2003 | Hardin et al. |
| 2003/0087242 A1 | 5/2003 | Mirkin et al. |
| 2003/0092005 A1 | 5/2003 | Levene et al. |
| 2003/0143724 A1 | 7/2003 | Cerrina et al. |
| 2004/0038331 A1 | 2/2004 | Reddy et al. |
| 2004/0152119 A1 | 8/2004 | Sood et al. |
| 2005/0001239 A1* | 1/2005 | Ishibashi ............... H01L 31/105 |
| | | 257/202 |
| 2005/0089298 A1 | 4/2005 | Maxwell et al. |
| 2005/0100919 A1* | 5/2005 | Stanton et al. .................... 435/6 |
| 2005/0201899 A1 | 9/2005 | Weisbuch |
| 2005/0208557 A1 | 9/2005 | Korlach et al. |
| 2005/0266424 A1 | 12/2005 | Hardin et al. |
| 2005/0275839 A1 | 12/2005 | Robinson et al. |
| 2006/0057606 A1 | 3/2006 | Korlach et al. |
| 2006/0062693 A1 | 3/2006 | Muraishi |
| 2006/0068506 A1 | 3/2006 | Uyeda et al. |
| 2006/0134666 A1 | 6/2006 | Korlach et al. |
| 2006/0160113 A1 | 7/2006 | Korlach et al. |
| 2006/0228722 A1 | 10/2006 | Kim et al. |
| 2007/0026447 A1 | 2/2007 | Korlach et al. |
| 2007/0036511 A1 | 2/2007 | Lundquist |
| 2007/0083122 A1* | 4/2007 | Alfano et al. ................. 600/476 |
| 2007/0141598 A1 | 6/2007 | Turner et al. |
| 2007/0172858 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0184475 A1 | 8/2007 | Hardin et al. |
| 2007/0238679 A1 | 10/2007 | Rank et al. |
| 2007/0269345 A1 | 11/2007 | Schilffarth et al. |
| 2007/0273290 A1* | 11/2007 | Ashdown ............... F21V 29/004 |
| | | 315/113 |
| 2007/0275395 A1 | 11/2007 | Hardin et al. |
| 2007/0292867 A1 | 12/2007 | Hardin et al. |
| 2008/0037008 A1 | 2/2008 | Shepard et al. |
| 2008/0050747 A1 | 2/2008 | Korlach et al. |
| 2008/0061683 A1 | 3/2008 | Bertram |
| 2008/0081769 A1 | 4/2008 | Hassibi |
| 2008/0087843 A1 | 4/2008 | Medintz et al. |
| 2008/0094632 A1* | 4/2008 | Harsh ........................ G01J 3/02 |
| | | 356/436 |
| 2008/0105831 A1 | 5/2008 | Reel et al. |
| 2008/0108082 A1 | 5/2008 | Rank et al. |
| 2008/0176769 A1 | 7/2008 | Rank et al. |
| 2008/0177139 A1 | 7/2008 | Courtney et al. |
| 2008/0199932 A1 | 8/2008 | Hanzel et al. |
| 2008/0227654 A1 | 9/2008 | Korlach et al. |
| 2008/0241833 A1 | 10/2008 | Williams |
| 2009/0015831 A1* | 1/2009 | Yguerabide et al. ......... 356/337 |
| 2009/0026978 A1* | 1/2009 | Robinson ........... H05B 37/0272 |
| | | 315/294 |
| 2009/0082212 A1 | 3/2009 | Williams |
| 2009/0087850 A1 | 4/2009 | Eid et al. |
| 2009/0137007 A1 | 5/2009 | Korlach et al. |
| 2009/0146076 A1 | 6/2009 | Chiou et al. |
| 2009/0170074 A1 | 7/2009 | Williams |
| 2009/0263797 A1 | 10/2009 | Zon |
| 2009/0275036 A1 | 11/2009 | Hardin et al. |
| 2009/0286245 A1 | 11/2009 | Bjornson et al. |
| 2009/0294813 A1* | 12/2009 | Gambino .......... H01L 27/14632 |
| | | 257/292 |
| 2009/0305278 A1 | 12/2009 | Hardin et al. |
| 2009/0312188 A1 | 12/2009 | Duer et al. |
| 2010/0009872 A1 | 1/2010 | Eid et al. |
| 2010/0035268 A1 | 2/2010 | Beechem et al. |
| 2010/0055666 A1 | 3/2010 | Wimberger-Friedl et al. |
| 2010/0065726 A1 | 3/2010 | Zhong et al. |
| 2010/0075328 A1 | 3/2010 | Bjornson et al. |
| 2010/0093068 A1 | 4/2010 | Williams |
| 2010/0121582 A1 | 5/2010 | Pan et al. |
| 2010/0255463 A1 | 10/2010 | Harsin et al. |
| 2010/0255487 A1 | 10/2010 | Beechem et al. |
| 2010/0256016 A1 | 10/2010 | Blair et al. |
| 2010/0256918 A1 | 10/2010 | Chen et al. |
| 2010/0262617 A1 | 10/2010 | Rothberg et al. |
| 2010/0304358 A1* | 12/2010 | Nie et al. ........................ 435/5 |
| 2010/0304367 A1 | 12/2010 | Hardin et al. |
| 2010/0317005 A1 | 12/2010 | Hardin et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0111401 A1 | 5/2011 | Korlach et al. |
| 2011/0130297 A1 | 6/2011 | Badorrek et al. |
| 2011/0210094 A1 | 9/2011 | Gray et al. |
| 2011/0223590 A1 | 9/2011 | Chiou et al. |
| 2011/0300534 A1 | 12/2011 | Chiou et al. |
| 2011/0306039 A1 | 12/2011 | Chiou et al. |
| 2011/0306143 A1 | 12/2011 | Chiou et al. |
| 2013/0004967 A1 | 1/2013 | Halverson et al. |

FOREIGN PATENT DOCUMENTS

| | | |
|---|---|---|
| EP | 1102782 B1 | 3/2006 |
| JP | 62-165129 | 7/1987 |
| JP | 04-303972 | 10/1992 |
| JP | 05-118991 | 5/1993 |
| JP | 2000-173093 | 6/2000 |
| JP | 2001-161696 | 6/2001 |
| JP | 2003-502847 | 1/2003 |
| JP | 2003-521684 A | 7/2003 |
| JP | 2003-295064 | 10/2003 |
| JP | 2003-532123 A | 11/2003 |
| JP | 2004-163257 A | 6/2004 |
| JP | 2004-219330 | 8/2004 |
| JP | 2004-523243 A | 8/2004 |
| JP | 2004-525342 | 8/2004 |
| JP | 2005-127795 A | 5/2005 |
| JP | 2005-156538 A | 6/2005 |
| JP | 2005-165256 | 6/2005 |
| JP | 2005172840 | 6/2005 |
| JP | 2006-220645 A | 8/2006 |
| JP | 2007-531527 A | 11/2007 |
| JP | 2008-520975 | 6/2008 |
| JP | 2009-511896 A | 3/2009 |
| JP | 2009-537148 A | 10/2009 |
| JP | 2013-522605 | 6/2013 |
| KR | 10-2010-0019409 | 2/2010 |
| WO | WO 8903432 A1 | 4/1989 |
| WO | WO 0036152 A1 | 6/2000 |
| WO | WO 01/42768 | 6/2001 |

(56) References Cited

FOREIGN PATENT DOCUMENTS

| | | |
|---|---|---|
| WO | WO 0036151 A9 | 8/2001 |
| WO | WO 01/84197 A1 | 11/2001 |
| WO | WO 0192501 A1 | 12/2001 |
| WO | WO 02/04680 A2 | 1/2002 |
| WO | WO 00/70073 A9 | 4/2002 |
| WO | WO 02/066683 | 8/2002 |
| WO | WO 02/072892 A1 | 9/2002 |
| WO | WO 02/073158 | 9/2002 |
| WO | WO-03/003015 | 1/2003 |
| WO | WO 03/064997 A2 | 8/2003 |
| WO | WO 2004011605 A2 | 2/2004 |
| WO | WO 2005/019419 A2 | 3/2005 |
| WO | WO 2005-080605 A2 | 9/2005 |
| WO | WO 2005/098042 A2 | 10/2005 |
| WO | WO 2006055521 A2 | 5/2006 |
| WO | WO 2006/073504 | 7/2006 |
| WO | WO 2007/091280 A1 | 8/2007 |
| WO | WO 2007/119067 | 10/2007 |
| WO | WO 2008/002101 | 1/2008 |
| WO | WO 2008016906 A2 | 2/2008 |
| WO | WO 2008/032096 | 3/2008 |
| WO | WO 2009/017678 | 2/2009 |
| WO | WO 2009/056065 | 5/2009 |
| WO | WO 2009/145818 | 12/2009 |

OTHER PUBLICATIONS

J. T. Blackard et al., "Intrahepatic cytokine expression is downregulated during HCV/HIV co-infection," Journal of Medical Virology, vol. 78, pp. 202-207 (2006).

J. Eid et al., "Real-time DNA sequencing from single polymerase molecules," Science, vol. 323, pp. 133-138 (2009).

K. Fife et al., "Multi-aperture image sensor with 0.7 μm pixels in 0.11 μm CMOS technology," IEEE Journal of Solid-State Circuits, vol. 43, No. 12, pp. 2990-3005 (2008).

T. D. Harris et al., "Single-Molecule DNA Sequencing of a Viral Genome," Science, vol. 320, pp. 106-109 (2008).

J. Korlach et al., "Selective aluminum passivation for targeted immobilization of single DNA polymerase molecules in zero-mode waveguide nanostructures," PNAS, vol. 105, No. 4, pp. 1176-1181 (2008).

M. J. Levene et al., "Zero-mode waveguides for single-molecule analysis at high concentrations," Science, vol. 299, pp. 682-686 (2003).

J. D. Levin, "Position-dependent effects of locked nucleic acid (LNA) on DNA sequencing and PCR primers," Nucleic Acids Research, vol. 34, No. 20, e142 (2006).

D. A. Neamen, Semiconductor Physics and Devices, pp. 17-19, McGrawHill, 1997.

C. Niclass et al., "A single photon avalanche diode array fabricated in deep-submicron CMOS technology," Proceedings of the conference on Design, automation and test in Europe: Proceedings, Munich, Germany, pp. 81-86 (2006).

J. Shendure et al., "Advanced sequencing technologies: methods and goals," Nat. Rev. Genet., vol. 5, pp. 335-344 (2004).

K. R. Spring et al., "Introduction to Fluorescence Microscopy," Nikon microscopy, 10 pages.

E. Stevens et al., "Low-crosstalk and low-dark-current CMOS image-sensor technology using a hole-based detector," Digest of technical Papers of 2008 IEEE International Solid-State circuits Conference, pp. 60-61 and p. 595 (2008).

S. M. Sze, Physics of Semiconductor Devices, pp. 674-675, Wiley, 2007.

T. Wang et al., "Single-molecule tracing on a fluidic microchip for quantitative detection of low-abundance nucleic acids," JACS, vol. 127, pp. 5354-5359 (2005).

C. Y. Zhang et al., "Single-quantum-dot-based DNA nanosensor," Nature Materials, vol. 4, pp. 826-831 (2005).

Notification of Transmittal of the International Search Report and the Written Opinion of the International Search Authority, or the Declaration, issued by International Search Authority, on Jun. 17, 2010, in a PCT application No. PCT/CN2010/070973.

N. G. Walter, et al., "Do-it-yourself guide: how to use the modern single-molecule toolkit," Nature Methods, vol. 5, pp. 475-489 (2008).

A. L. McGuire et al., "The future of personal genomics," Science, vol. 317, p. 1687 (2007).

I. L. Medintz et al., "Quantum dot bioconjugates for imaging, labelling and sensing," Nature Materials, vo. 4, pp. 435-446 (2005).

M. Schena, "Microarray Biochip Technologies," p. 28 and pp. 76-78 (2000).

J. Shendure et al., "Accurate multiplex polony sequencing of an evolved bacterial genome," Science, vol. 309, pp. 1728-1732 (2005).

Office Action, issued in corresponding U.S. Appl. No. 12/801,503, dated Aug. 1, 2012, 8 pages.

Office Action, issued in corresponding U.S. Appl. No. 12/805,411, dated Aug. 6, 2012, 21 pages.

Examiner's First Report issued by the Australian Patent Office, dated Jun. 20, 2011, in an Australian patent application No. 2010249264 (2 pages).

International Search Report and Written Opinion, issued by International Searching Authority, dated Jul. 7, 2011, in International application No. PCT/CN2011/071814 (14 pages).

Kamtekar et al., "Insights into Strand Displacement and Processivity from the Crystal Structure of the Protein-Primed DNA Polymerase of Bacteriophage φ29," Mol Cell, vol. 16, pp. 609-618 (2004).

Kim et al., "Crystal structure of *Thermus aquaticus* DNA polymerase," Nature, vol. 376, pp. 612-616 (1995).

Moerner et al., "Review Article: Methods of single-molecule fluorescence spectroscopy and microscopy," Review of Scientific Instruments, vol. 74, No. 8, pp. 3597-3619 (2003).

Tessier et al., "Ligation of single-stranded oligodeoxyribonucleotides by T4 RNA ligase," Anal. Biochem., vol. 158, pp. 171-178 (1986).

Clarke et al., "Continuous base identification for single-molecule nanopore DNA sequencing" Nature Nanotechnol. 4:265-270 (2009).

Dorre et al. "Techniques for Single Molecule Sequencing" *BioImaging* 5: 139-152 (1997).

Fidalgo Da Silva and Reha-Krantz "DNA polymerase proofreading: active site switching catalyzed by the bacteriophage T4 DNA polymerase" *Nucl. Acids Res.* 35(16):5452-5463 (2007).

Goodwin et al. "Application of Single Molecule Detection to DNA Sequencing" *Nucleos. Nucleot.* 16:543-550 (1997).

Guo et al. (2010) "An Integrated System for DNA Sequencing by Synthesis Using Novel Nucleotide Analogues" *Accounts of Chemical Research*, 43(4):551-63.

Howorka et al. "Sequence-specific detection of individual DNA strands using engineered nanopores" *Nat. Biotechnol.* 19:636-639 (2001).

Hyman "A New Method of Sequencing DNA" *Anal. Biochem.* 174:423-436 (1968).

Reddy et al. "Processive Proofreading is Intrinsic to T4 DNA Polymerase" *J. Biol. Chem.* 267(20):14157-14166 (1992).

Reha-Krantz "Regulation of DNA Polymerase Exonucleolytic Proofreading Activity: Studies of Bacteriophage T4 'Antimutator' DNA Polymerases" *Genetics* 148:1551-1557 (1998).

Ronaghi et al. "A Sequencing Method Based on Real-Time Pyrophosphate" *Science* 281:363-365 (1998).

Sauer et al. "Detection and identification of single dye labeled mononucleotide molecules released from and optical fiber in a microcapillary: First steps towards a new single molecule DNA sequencing technique" *Phys. Chem. Chem. Phys.* 1(10):2471-2477 (1999).

Turcatti et al. (2008) "A new class of cleavable fluorescent nucleotides: synthesis and optimization as reversible terminators for DNA sequencing by synthesis" *Nucleic Acids Res.*, 36(4):e25, doi: 10.1093/nar/gkn021, published online Feb. 7, 2008.

(56) References Cited

OTHER PUBLICATIONS

English translation of Notice of Reasons for Rejection issued by Japanese Patent Office, mailed Dec. 3, 2013, in Japanese Patent Application No. JP2013-501618 (4 pages).
Notification of Reason(s) for Rejection, issued by Japanese Patent Office, mailed Jul. 23, 2014, in Japanese Patent Application No. 2011-288867 (7 pages including translation).
Anker et al., "Magnetically-modulated Optical Nanoprobes (MagMOONs) and Systems," Journal of Magnetism and Magnetic Materials 293:655-662 (2005).
Cao, Y.M. et al., "DNA-modified core-shell Ag/Au nanoparticles," J. Am. Chem. Soc., vol. 123, pp. 7961-7962 (2001).
Cheng "High-Speed DNA-Sequence Analysis" Prog. Biochem. Biophys. 22:223-227 (1995) (English abstract on p. 227).
Dapprich et al. "DNA Attachment to Optically Trapped Beads in Microstructures Monitored by Bead Displacement" Bioimaging 6:25-32 (1998).
Han et al., "High performance electrophoresis system for site-specific entrapment of nanoparticles in a nanoarray," Proc. of SPIE 7574:75740L (2010).
Kang et al., "Synthesis and Characterization of Nanometer-Size $Fe_3O_4$ and $\gamma$-$Fe_2O_3$ Particles," Chem. Mater. 8(9):2209-2211 (1996).
McNaughton et al., "Fabrication of uniform half-shell magnetic nanoparticles and microspheres with applications as magnetically modulated optical nanoprobes," Submitted to Applied Physics Letters, Jun. 16, 2005; 6 pp. [online]; retrieved from the Internet: http://arxiv.org/abs/cond-mat/0506418.
Metzker "Sequencing technologies—the next generation," Nature Reviews Genetics 11:31-46 (2010).
Nandwana et al., "Size and Shape Control of Monodisperse FePt Nanoparticles," J. Phys. Chem. C 111(11):4185-4189 (2007).
Ozsolak et al., "Direct RNA sequencing," Nature 461:814-818 (2009).
Park et al., "Multifunctional Nanoparticles for Photothermally Controlled Drug Delivery and Magnetic Resonance Imaging Enhancement," Small 4(2):192-196 (2008).
Perro et al., "Design and synthesis of Janus micro- and nanoparticles," J. Mater. Chem. 15:3745-3760 (2005).
Qiu et al., "Fluorescence single-molecule counting assays for high-sensitivity detection of cytokines and chemikines," Clin. Chem. 53(11):2010-2012 (2007).
Ramadan et al., "Customized trapping of magnetic particles," Microfluidics and Nanofluidics 6(1):53-62 (2009).
Schmitt et al., "High-Refractive-Index Waveguide Platforms for chemical and biosensing," in Optical Guided-Wave Chemical and Biosensors I. M. Zourob and A. Lakhtakia (Eds.), 2010; pp. 7 and 21.
Velev et al., "Particle-localized AC and DC manipulation and electrokinetics," Ann. Rep. Prog. Chem., Sect. C 105:213-246 (2009).
Wang et al., "One-Pot Synthesis and Bioapplication of Amine-Functionalized Magnetite Nanoparticles and Hollow Nanospheres," Chem. Eur. J. 12:6341-6347 (2006).
Wu et al., "Bioinspired Nanocorals with Decoupled Cellular Targeting and sensing Functionality," Small 6(4):503-507 (Feb. 22, 2010).
Zheng et al., "Quasicubic $\alpha$-$Fe_2O_3$ Nanoparticles with Excellent Catalytic Performance," J. Phys. Chem. B 110(7) (2006).
Office Action (Patent Examination Report No. 1) dated Oct. 15, 2012, issued in Australian Patent Application No. 2011229691.
Examiner's Report dated Apr. 5, 2013, issued in Canadian Patent Application No. 2,763,100.
English translation of Office Action (Notice to Submit a Response) dated Apr. 2, 2013, issued in Korean Patent Application No. 10-2011-7031724 (4 pages).
English translation of Notification of Reason(s) for Refusal, issued by Japanese Patent Office, mailed Jul. 2, 2013, in Japanese Patent App. No. 2011-288867 (4 pages).
Notification of Reason(s) for Rejection, issued by Japanese Patent Office, mailed Jun. 10, 2014, in Japanese Patent Application No. 2013-512746 (10 pages including translation).
European Office Action, issued by European Patent Office, dated May 13, 2014, in European Patent Application No. 10 196 884.0-1554 (9 pages).
Abramova et al., "Design and synthesis of dinucleotide 5'-triphosphates with expanded functionality," Bioorganic & Medicinal Chemistry, 16, pp. 9127-9132 (2008).
Metwalli et al., Surface characterization of mono-, di-, and tri-aminosilane treated glass substrate, *J. of Colloid and Interface Science*, 298:825-831 (2006).
Japanese Office Action for application No. 2011-553266, dated Mar. 3, 2014, 8 pgs.
Lehmuskero, et al., "Refractive index and extinction coefficient dependence of thin Al and Ir films on deposition technique and thickness," Optics Express, vol. 15, No. 17, pp. 10744-10752. Aug. 20, 2007.
Notice of Reasons for Rejection issued by Japanese Patent Office dated Oct. 25, 2016, in Japanese Patent Application No. 2015-236536.
Notice of Reason for Rejection issued by the Japanese Patent Office on Feb. 2, 2017 in counterpart Japanese Application No. 2015-236536.

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ctcccggggc actcgcaagc                                               20

<210> SEQ ID NO 2
<211> LENGTH: 27
<212> TYPE: DNA
<213> ORGANISM: Artificial Sequence
<220> FEATURE:
<223> OTHER INFORMATION: primer

<400> SEQUENCE: 2
tttggtcctt gtcttatgtc cagaatg                                       27

<210> SEQ ID NO 3
<211> LENGTH: 34
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: n is G modified with FAM
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (34)..(34)
<223> OTHER INFORMATION: n is C modified with DABCYL

<400> SEQUENCE: 3
nctagcattt gggcgtgccc ccgcaagagc tagn                               34

<210> SEQ ID NO 4
<211> LENGTH: 34
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (1)..(1)
<223> OTHER INFORMATION: n is G modified with HEX
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (34)..(34)
<223> OTHER INFORMATION: n is C modified with DABCYL
```

```
<400> SEQUENCE: 4
nctagcattt gggcgtgccc ccgcaagagc tagn                                    34
```

APPARATUS AND METHOD FOR DETECTION AND DISCRIMINATION MOLECULAR OBJECT

RELATED APPLICATIONS

This application claims the benefit of priority to U.S. Provisional Patent Application No. 61/159,310, filed Mar. 11, 2009, the entire content of which is incorporated by reference herein in its entirety.

TECHNICAL FIELD

The present invention relates to a detecting apparatus, and the method of using this apparatus to detect and/or discriminate an object. Further relates to a detecting apparatus that is able to detect and/or discriminate an object emitting a light of low intensity.

BACKGROUND

The Human Genome Project (HGP) spurred a great increase in sequencing throughput and resulted in a corresponding drop in sequencing costs. In contrast to the 13 years and cost of nearly three billion US dollars, per genome sequencing costs have been reduced significantly—indeed two individual genomes have recently been completed (McGuire et al., *Science* 317:1687 (2007)). Personal genomes represent a paradigm shift in medical treatment for both patients and health care providers. By managing genetic risk factors for disease, health care providers can more readily practice preventative medicine and provide customized treatment. With large banks of completed genomes, drug design and administration can be more efficient, pushing forward the nascent field of pharmacogenomics.

Many conventional DNA sequencing technologies implement optoelectronic technique as a means to detect and/or discriminate an object by detecting light emitted from the object. A detecting apparatuses used in these technologies are often expensive and the efficiencies are not high.

Conventional methods are usually based on the measurement within a certain wavelength band where the light emitted from the object(s) being detected has the highest intensity. The measured intensity is then used to calculate the concentration or amount of the objects. Recently, detecting light emitted from a single object is becoming popular. For example, one may need to detect the fluorescent light emitted from a single dye molecule so as to, e.g., discriminate the molecule. The intensity of such a fluorescent light can be very low, such that conventional detecting apparatuses and methods are not suitable to detect such a weak light. Also, the sensitivity of analytical procedures such as flow cytometry and flow-cytometry-like microfluidic lab-on-a-chip device can be limited by the sensitivity of the light detector. Increasing the sensitivity of such procedures could allow them to detect materials present at relatively low levels which nonetheless may be of interest in, for example, diagnostic or research applications.

Moreover, in many conventional apparatuses, color filters are often used, allowing a portion of the emitted light within a certain wavelength band to pass through and blocking other portion of the emitted light. Therefore, the apparatuses are complicated and more space is needed. Besides, since part of the emitted light is blocked by the color filter, the number of photons reaching the light detector is reduced. This makes such conventional apparatuses and methods even less suitable for detecting and/or discriminating, e.g., object with weak emission.

Therefore, there is a need for an apparatus and a method to detect and/or discriminate an object, especially an object emitting light of low intensity such as a single dye molecule.

SUMMARY OF THE INVENTION

In accordance with the invention, there is provided an apparatus for detecting an object capable of emitting light. The apparatus comprises a light detector comprising at least a first optical sensor and a second optical sensor capable of determining the intensity of the light; and a computer processing output signal generated by the optical sensors and comparing a result of the processing with a known result corresponding to a known type to determine whether the object belongs to the known type.

Also in accordance with the invention, there is provided a method for detecting an object capable of emitting light. The method comprises providing a light detector comprising at least a first optical sensor and a second optical sensor, wherein the light detector absorbs light emitted from the at least one object; processing output signal generated by the at least two optical sensors; and comparing at least one result of the processing with at least one known result corresponding to at least one known type to determine whether the at least one object belongs to the at least one known type.

Also in accordance with the invention, there is provided a non-transitory computer-readable medium encoded with a computer program product. The computer program product, when executed by a computer, instructed the computer to process output signal generated by at least a first optical sensor and a second optical sensor, wherein the signals is generated in response to absorbing light emitted from an object; and to compare a result of the processing with a known result corresponding to a known type to determine whether an object belongs to the known type.

Also in accordance with the invention, there is provided a method of sequencing a nucleic acid, comprising the steps of: (a) performing single molecule nucleic acid sequencing of the at least one nucleic acid molecule, wherein the single molecule nucleic acid sequencing leads to emission of light correlated to the identity of at least one base comprised by the nucleic acid; (b) detecting said light with at least one light detector comprising at least a first optical sensor and a second optical sensor; (c) processing signal output from the at least two optical sensors; and (d) comparing at least one result of the processing with at least one known result corresponding to at least one known type to determine an identity of at least one base comprised by the nucleic acid.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

DETAILED DESCRIPTION

Figure 1:
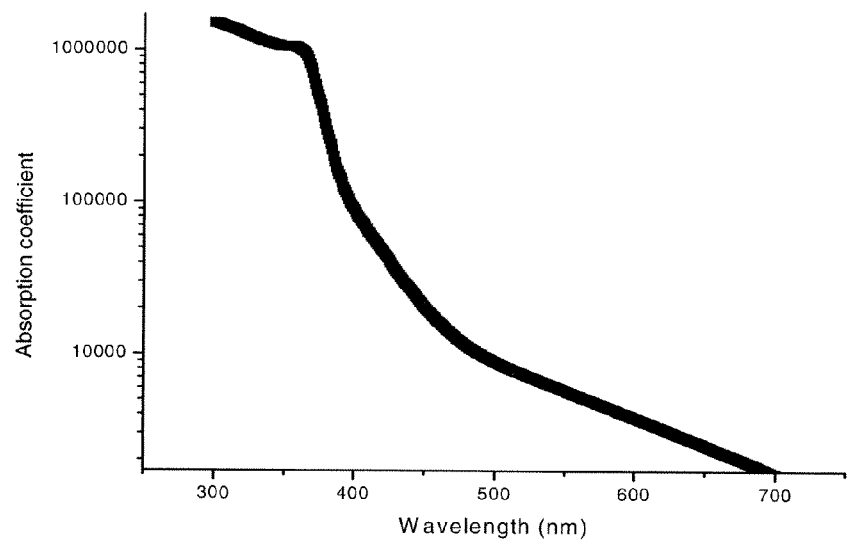
FIG. 1 is a graph showing the absorption coefficient of silicon.

Embodiments consistent with the present invention include a detecting apparatus for detecting and/or discriminating an object. The detecting apparatus is capable of detecting weak light emitted from the object.

Hereinafter, embodiments consistent with the present invention will be described in detail with reference to drawings. Wherever possible, the same reference numbers will be used throughout the drawings to refer to the same or like parts.

1. APPARATUS OF THE INVENTION

The detecting apparatus consistent with the present invention can be used to detect and/or discriminate an object, which is capable of emitting light. The object may be a source of luminescence, such as a fluorescent dye molecule, a phosphorescent dye molecule, a quantum dot, or a luminescent product (e.g., an excited-state reaction product such as singlet oxygen or excited coelenteramide) of a bioluminescent or chemiluminescent system. An apparatus of the invention may or may not comprise at least one source of excitatory light, such as at least one laser. A source of excitatory light is not needed to detect objects which luminesce independently of light absorption, such as can be generated via bioluminescence or chemiluminsescence, for example. The object may also be a target molecule without light emitting capability, but may be attached to a labeling object which is capable of emitting light (e.g., a fluorescent dye molecule, a phosphorescent dye molecule, or a quantum dot). A certain labeling object may be capable of being attached to a specific target molecule. Thus, the target molecule may be identified via the labeling object. More than one labeling object may be attached to one target molecule. The apparatus may also be used to monitor a large number of objects.

The detecting apparatus consistent with the present invention may comprise a light detector detecting light emitted from the object. The light detector is capable of at least partially absorbing light incident thereon and generating output signals in response to the light. The light detector may comprise a control circuit for controlling the operation of the light detector. The control circuit may comprise a circuit of signal amplifier, A/D convertor, integrator, comparator, logic circuit, readout circuit, memory, microprocessor, clock, and/or address.

The detecting apparatus may comprise a computer for processing output signals from the light detector and generating a determination result. The detecting apparatus may further comprise a blind sheet with a pinhole. The detecting apparatus may also comprise a linker site to which the object may be attached. The linker site may be formed in the pinhole or be formed outside but proximate to the pinhole. The apparatus may further comprise an excitation light source. The object may absorb light emitted from the excitation light source and then emit another light to be detected by the detecting apparatus. The light emitted from the object may have different wavelength than the light emitted from the excitation light source.

1.1 Optical Sensor

The light detector consistent with the present invention may comprise a plurality of optical sensors. An optical sensor consistent with the present invention may be, e.g., a photodiode, an avalanche photodiode (APD), a phototransistor, a photogate, a quantum-well infrared photodetector (QWIP), a thin-film on ASIC (TFA), a metal-semiconductor-metal (MSM) photodetector, or a combination thereof. In one embodiment of the present invention, the optical sensor may be a photodiode.

A photodiode is a solid-state device which converts light into electric current or voltage. A photodiode is usually made of semiconductor materials, such as silicon. The basic structure of a photodiode comprises a p-n junction formed by joining a p-type semiconductor and an n-type semiconductor. A photodiode may have only one p-n junction and provide only one output signal, therefore be considered as one optical sensor; a multi-junction photodiode has more than one p-n junction and may provide more than one output signal, wherein each p-n junction may be considered as one optical sensor.

Alternatively, a photodiode may be a p-i-n photodiode. The p-i-n photodiode is a special type of p-n junction photodiode with an intrinsic layer, or a lightly-doped n-type layer, or a lightly-doped p-type layer, sandwiched between the n-type layer and the p-type layer. In a p-i-n photodiode, the thickness of the depletion region, which is almost the whole intrinsic layer, can be tailored to optimize the quantum efficiency and frequency response. (S. M. Sze, Physics of Semiconductor Devices, pp. 674-675, Wiley, 2007).

P-type semiconductor and n-type semiconductor may be formed by doping p-type impurities and n-type impurities into a semiconductor substrate, respectively. For example, in silicon, phosphorus or arsenic may act as n-type impurities, and boron and indium may act as p-type impurities. Generally, two methods may be used to introduce impurities into a semiconductor substrate: diffusion and ion implantation. By diffusing or implanting p-type impurities into an n-type semiconductor substrate, portion of the n-type semiconductor substrate may be converted to p-type semiconductor. Accordingly, a p-n junction may be formed. Alternatively, by diffusing or implanting n-type impurities into an p-type semiconductor substrate, portion of the p-type semiconductor substrate may be converted to n-type semiconductor, and thus a p-n junction may be formed. Other than diffusion and ion implantation, epitaxial growth may also be used to fabricate n-type semiconductor or p-type semiconductor, which is a process that a thin, single crystal layer is grown on the surface of a single crystal substrate. (D. A. Neamen, Semiconductor Physics & Devices, pp. 17-18, McGrawHill, 1997). When a light is incident on a photodiode, electron-hole pairs may be generated in the photodiode. If an electron-hole pair is generated in the depletion region of the photodiode, the built-in potential in the depletion region may separate the electron and the hole and thus generate either photocurrent or voltage.

Different photodiodes may have different capabilities of absorbing an incident light. The capability can be described by the absorption coefficient α of the material constituting the photodiode. FIG. 1 shows the absorption coefficient of silicon at different wavelengths. The photon flux φ of the incident light decreases exponentially with the depth that the light penetrates into the photodiode. The photon flux at a depth x inside the photodiode can be expressed as:

$$\phi(\lambda, x) = \phi_0(\lambda) \cdot e^{-\alpha x}$$

where λ is the wavelength of the incident light and $\phi_0$ is the photon flux at the surface of the photodiode. Therefore, the photon flux absorbed in the depletion region can be given by:

$$\Delta\phi(\lambda) = \phi_0(\lambda) \cdot (e^{-\alpha xu} - e^{-\alpha xl})$$

where xu and xl are the depths of the upper and lower boundaries of the depletion region, respectively.

The photon flux absorbed in the depletion region may be converted to a photocurrent as an output signal of the photodiode. The photocurrent can be represented by:

$$I_{PD}(\lambda) = 1.98 \times 10^{-16} \cdot A \cdot [\phi_0(\lambda) \cdot R(\lambda)/\lambda]$$

where A is the area of the optical window, and R(λ) is the responsivity of a photodiode, which is defined as the amount of photocurrent produced by a unit power of incident light.

1.2 Computer for Signal Processing

Consistent with the present invention, a computer is provided which is able to process output signals generated by the light detector by performing a mathematic or logic operation on the output signals, and to determine the presence and type of an object. The computer used for processing output signals from an optical sensor may be, for example, a personal computer, a microprocessor-based or programmable consumer electronics, a logic circuit, or the like.

The computer may comprise one or more storage devices that temporarily or permanently store data and computer program containing software codes representing an algorithm. The computer may perform processing based on the algorithm. The storage device may be a read-only memory (ROM), a random access memory (RAM), or a memory with other access options. The storage device may be physically implemented by computer-readable media, such as, for example: (a) magnetic media, like a hard disk, a floppy disk, or other magnetic disk, a tape, a cassette tape; (b) optical media, like optical disk (CD-ROM, digital versatile disk—DVD); (c) semiconductor media, like DRAM, SRAM, EPROM, EEPROM, memory stick, or by any other media, like paper.

The computer may comprise one or more interfaces for receiving output signals from the light detector. The computer may comprise one or more processors for processing these signals.

Moreover, the computer may comprise one or more input devices for receiving commands from a user, and may comprise one or more output devices for outputting the processing results. The input device may be, for example, a mouse, a keyboard, or a control panel having a plurality of buttons. The output device may be, for example, a display or a printer.

1.3 Exemplary Detecting Apparatuses

Figure 2:
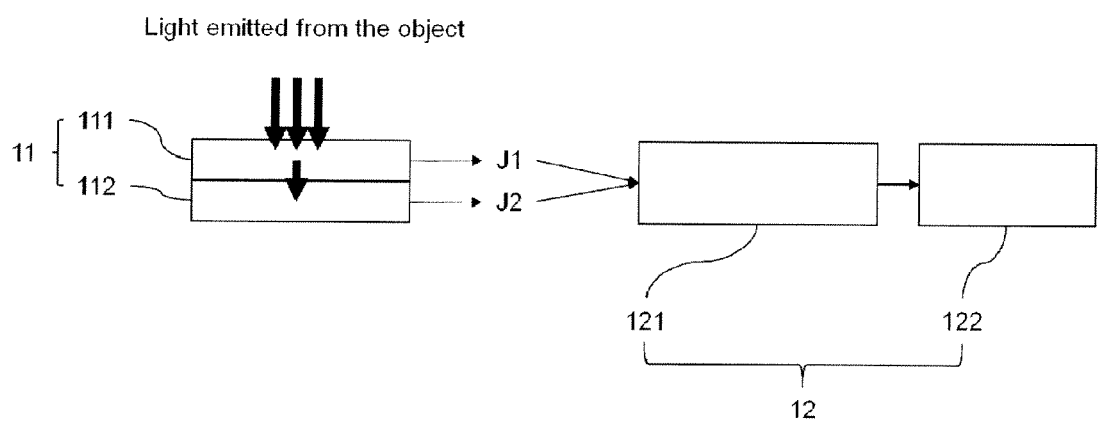
FIG. 2 is a view showing a detecting apparatus consistent with the present invention.

Referring to FIG. 2, a detecting apparatus 1 consistent with the present invention is illustrated. The detecting apparatus 1 may comprise a light detector 11 and a computer 12.

Figure 3:
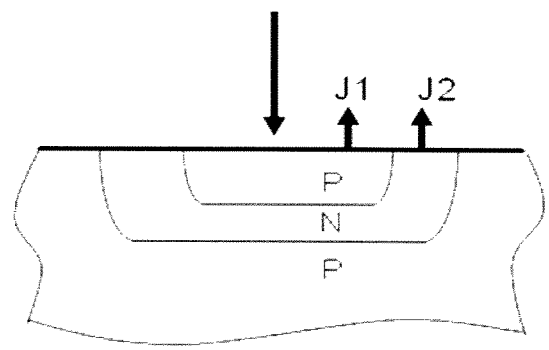
FIG. 3 is a view showing a light detector consistent with the present invention.

The light detector 11 may comprise a first optical sensor 111 and a second optical sensor 112. In some embodiments, the light detector 11 may comprise more than two optical sensors. For example, in some embodiments, the light detector 11 may comprise three optical sensors or four optical sensors. The first optical sensor 111 and the second optical sensor 112 may be stacked. In the stacked configuration, light emitted from an object passes through the first optical sensor 111, and then passes through the second optical sensor 112. In some embodiments, the optical sensors may be vertically or substantially vertically stacked. In other embodiments, the optical sensors may be obliquely stacked in a direction at a certain angle (such as 10°, 30°, 45°, 60°, etc.) with respect to the vertical direction. In some embodiments, the light detector 11 may be a multi-junction photodiode comprising a plurality of p-n junctions formed therein. In a multi-junction photodiode, each p-n junction may form the basic structure of one individual optical sensor. Each of the first optical sensor 111 and the second optical sensor 112 may comprise, for example, one p-n junction in the multi-junction photodiode, respectively, as shown in FIG. 3.

Figure 4:
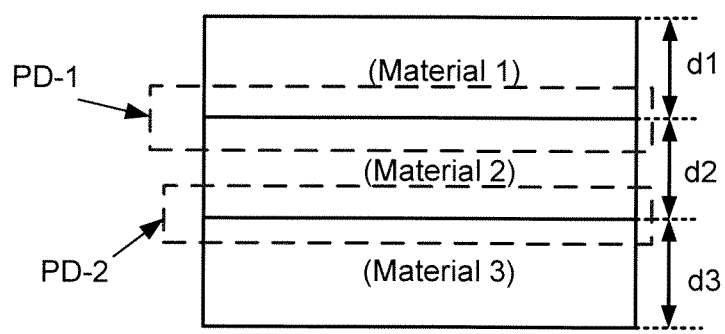
FIG. 4 is a view showing a light detector consistent with the present invention.

In some embodiments, different optical sensors in the light detector 11 may be made of same semiconductor material, such as silicon, germanium, GaAs AlGaAs, InGaAs, InGaAsN, InGaP, CdTe, or CdS. In some embodiments, different optical sensors in the light detector 11 may be made of different semiconductor materials. For example, FIG. 4 shows a light detector formed of two vertically stacked optical sensors PD-1 and PD-2. Optical sensors PD-1 is made of material-1 and material-2 while PD-2 is made of material-2 and material-3. Material-1, material-2, and material-3 may be a combination of the semiconductor materials mentioned above. In addition, the thickness of these optical sensors may also be different.

As shown in FIG. 2, light emitted from an object, e.g., a quantum dot (QD) incident on the light detector 11 may be partially absorbed by the first optical sensor 111, generating a first signal J1. Unabsorbed light passes through the first optical sensor 111 and may then be partially absorbed by the second optical sensor 112, generating a second signal J2. These signals may be sent to the computer 12 for processing.

In some embodiments, light emitted from an object may be incident on the light detector 11 without passing through another optical element, such as an optical filter, a prism, or a lens (i.e., may be directly incident on the light detector). In some embodiments, the apparatus may further comprise a light collecting optical structure for collecting the light emitted from the object.

In some embodiments, the light detector 11 may comprise two or more optical sensors arranged horizontally (not shown). In these embodiments, the detecting apparatus 1 may further comprise an optical structure placed between the object and the light detector 11. The light emitted from the object may be directed by the optical structure to one or more of the optical sensors and partially absorbed by the one or more of the optical sensors. The direction of light after passing through the optical structure may be different for light with different wavelength. Therefore, different optical sensors in the light detector with horizontal arrangement may detect light with different wavelengths.

Figure 5:
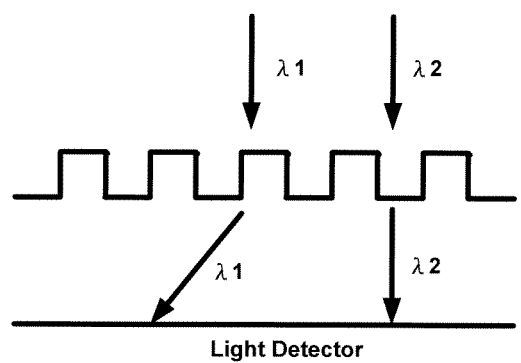
FIG. 5 is a view showing a grating used in a detecting apparatus consistent with the present invention.

In some embodiments, the optical structure may comprise a prism. In some embodiments, the optical structure may comprise a lens. In some embodiments, the optical structure may comprise a prism and a lens. The prism may be, e.g., a triangular prism, an Abbe prism, a Pellin-Broca prism, an Amici prism, or a combination thereof. The lens may be, e.g., a converging lens, a diverging lens, or a combination thereof. The optical structure may be made from, e.g., glass, plastic, or other materials that are transparent to the wavelengths of interest. The transparency of the optical structure may be high enough to allow the majority of the light to pass through the optical structure Alternatively, in some embodiments, the optical structure may comprise a grating. The grating may be, e.g., a binary grating, a blaze grating, a sinusoidal grating, a multi-level grating, a volume grating, or a combination thereof. FIG. 5 shows as an example a detecting apparatus consistent with one embodiment of the present invention. In this detecting apparatus, the light detector comprises a plurality of optical sensors horizontally arranged at different positions. A grating may be used to direct light of different wavelengths from an object to different positions of the light detector so as to be absorbed by different optical sensors.

Consistent with the present invention, a detecting system may be provided comprising an array of the detecting apparatuses consistent with the present invention. Consistent with the present invention, a detecting system may also be provided comprising an array of the light detectors consistent with the present invention and a computer for processing output signals from the array of light detectors and performing detection and/or discrimination based on the processing result. Such detecting systems may detect and/or discriminate a plurality of objects at one time, and thus may be suitable for large-scale parallel sequencing of nucleic acids, for example.

The computer 12 may comprise a processing unit 121 and an output unit 122. The processing unit 121 processes the output signals from the light detector 11 and determines the presence and type of an object. Output unit 122 outputs the determination result. In some embodiments, the computer 12 may also comprise a storage device (not shown), storing a computer program. The computer program may contain software codes for instructing the computer to process the signals.

The light detector 11 and computer 12 may be integrated into a single piece of semiconductor chip. The light detector 11 and computer 12 may be formed on separated semiconductor chips.

2. METHODS OF DETECTION

Figure 6:
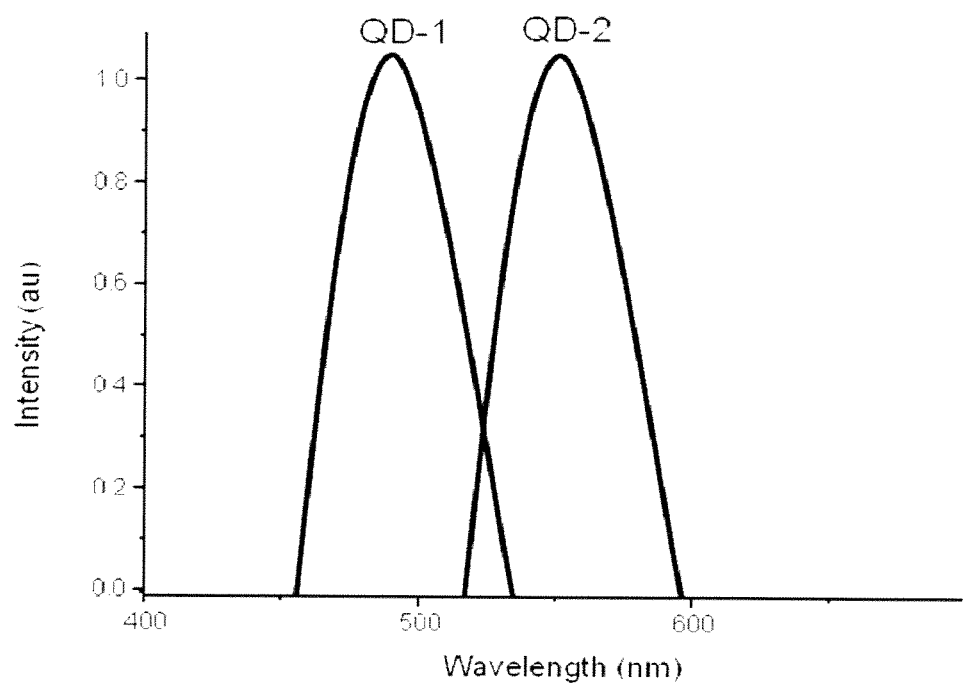
FIG. 6 is a graph showing the emission spectra of two quantum dots.

Light emitted from different objects may have different spectra. For example, FIG. 6 shows the emission spectra of two quantum dots ("QDs") (QD-1 and QD-2) as two objects. In this example, the peaks of these two emission spectra are at different wavelengths. In other examples, the emission spectra of different objects may also have different shapes.

Figure 7:
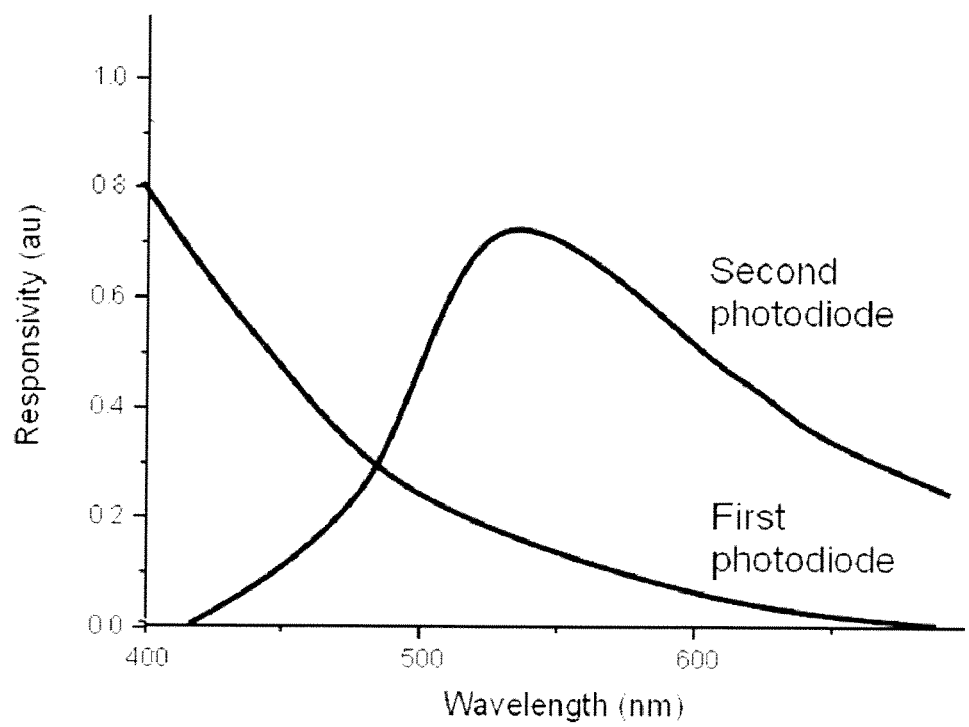
FIG. 7 is a graph showing the responsivity curves of two photodiodes consistent with the present invention.

The first optical sensor 111 and the second optical sensor 112 may have different responsive properties. FIG. 7 shows, as an example, the responsivity curves of the first optical sensor 111 and the second optical sensor 112. The responsivities of the first optical sensor 111 and the second optical sensor 112 may differ from each other in that they have different shapes and/or they may peak at different wavelengths.

Figure 8:
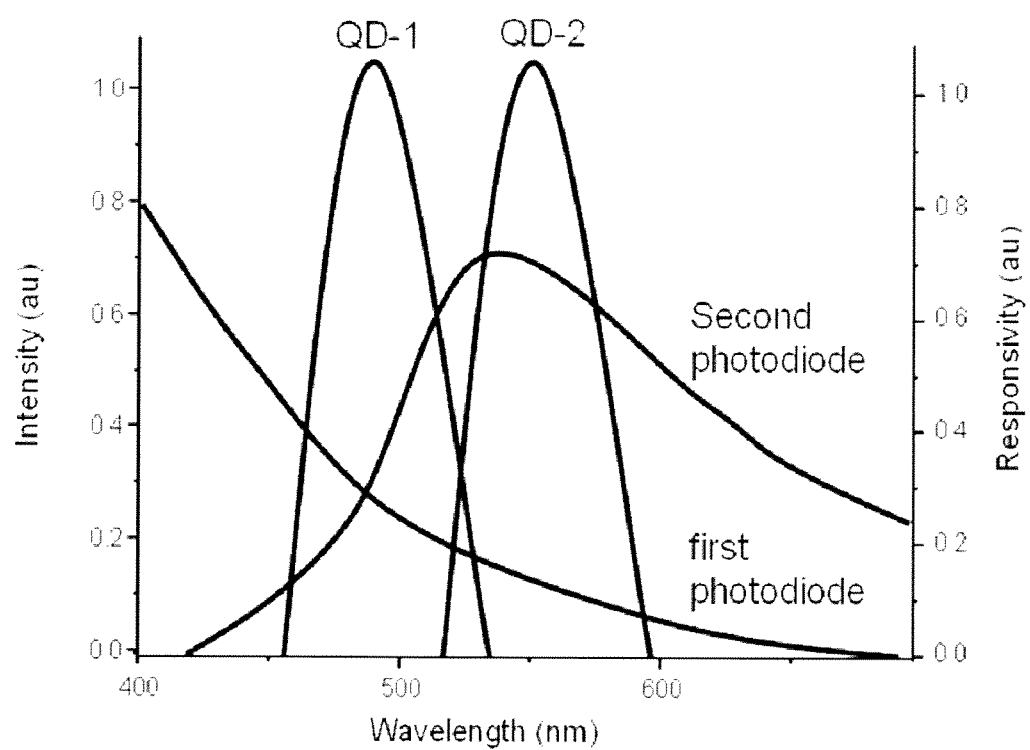
FIG. 8 is a graph showing the spectra of two quantum dots and the responsivity curves of two photodiodes in one figure.

For clearer illustration, FIG. 8 shows the responsivity curves of two optical sensors and the emission spectra of two QDs in one figure. In this example, light emitted from QD-1 may generate signals of similar strength at the two optical sensors. On the other hand, light emitted from QD-2 may generate a signal at the second optical sensor 112 stronger than that at the first optical sensor 111.

In some embodiments, as shown in FIG. 2, light emitted from an object may be incident on the light detector 11 and partially absorbed by the first optical sensor 111 and the second optical sensor 112, which in turn generate signals J1 and J2, respectively. The computer 12 processes the signals J1 and J2, and discriminates the object.

Figure 9:
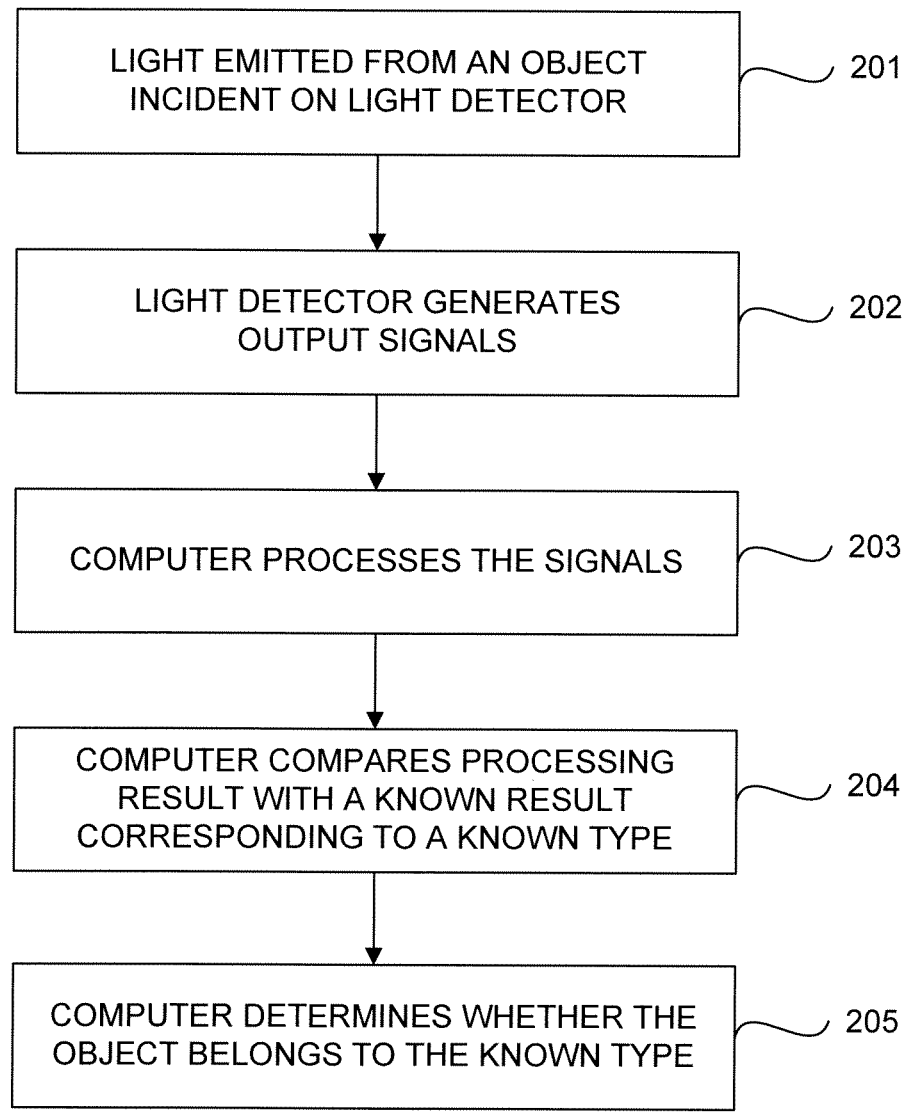
FIG. 9 is a flow chart illustrating a detecting method according to one embodiment of the invention.

FIG. 9 shows a flow chart of a method for discriminating an object according to one embodiment of the present invention. At step 201, a light emitted from an object is incident on the light detector 11. At step 202, two output signals J1 and J2 are generated by the first optical sensor and the second optical sensor, respectively, and the signals J1 and J2 are sent to the computer 12. At step 203, the computer 12 processes the signals J1 and J2. At step 204, the computer 12 compares the processing result with a known result corresponding to a known type of object. At step 205, the computer 12 determines whether the object belongs to the known type.

In one embodiment, processing the signals J1 and J2 may comprise calculating a ratio of J1 and J2. If the calculated ratio is within a certain range corresponding to the known type of object, it may be determined that the object being detected belongs to the known type. For example, a known type of quantum dot QD-1 may have a corresponding range of 0.7<J2/J1<1.2. If the calculated ratio for an object being detected is 0.9, it may be determined that the object is a QD-1 type object.

Figure 10:
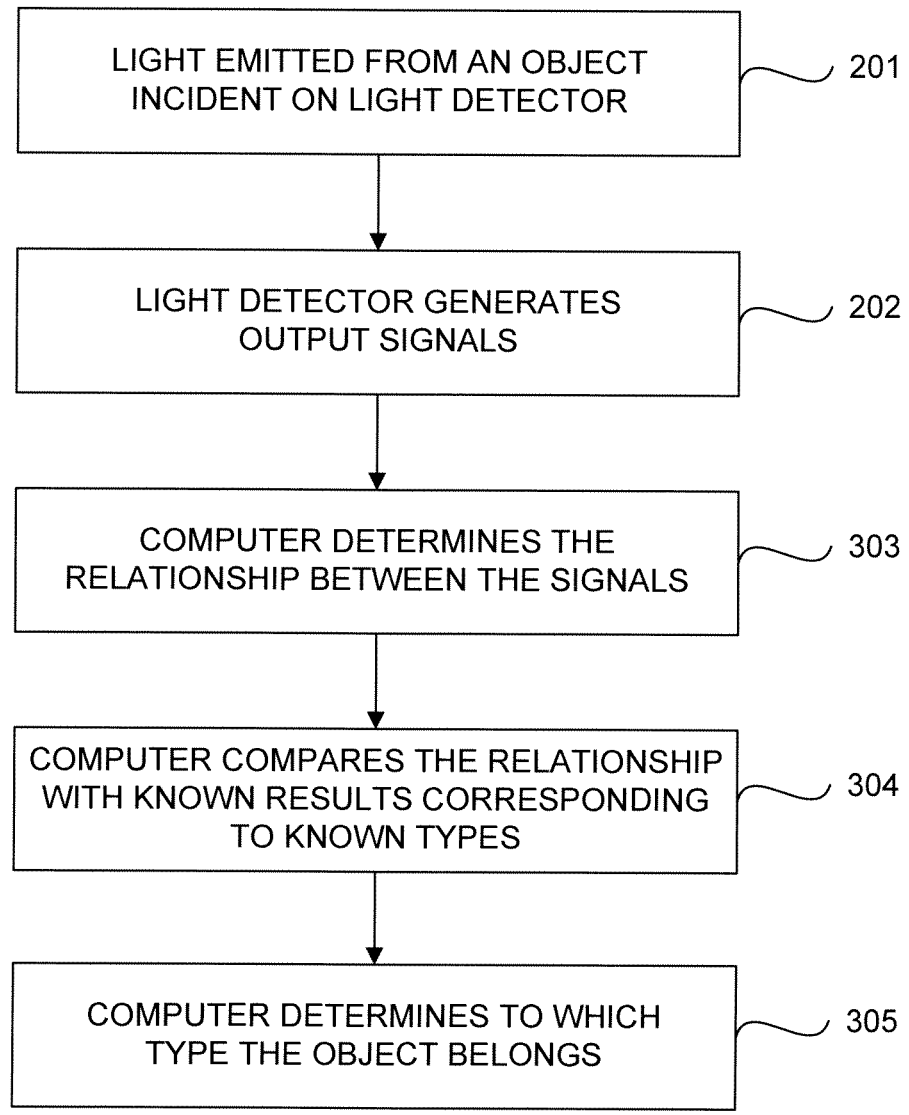
FIG. 10 is a flow chart illustrating a detecting method according to another embodiment of the invention.

FIG. 10 shows a flow chart of a method for discriminating an object according to another embodiment of the present invention. In this embodiment, an object may be determined to belong to one of, e.g., three known types of object, i.e., Type 1, Type 2, and Type 3. The first two steps of this embodiment may be the same as those in the above-noted embodiment. At step 303, the computer 12 determines the relationship between these two signals J1 and J2. At step 304, the computer 12 compares the relationship with known results corresponding to known types of object. At step 305, the computer 12 determines to which type the object belongs based on the comparison result.

In this embodiment, for example, if J1>J2, then the object may be determined to be a Type 1 object. If J1≈J2, then the object may be determined to be a Type 2 object. If J1<J2, then the object may be determined to be a Type 3 object.

Figure 11:
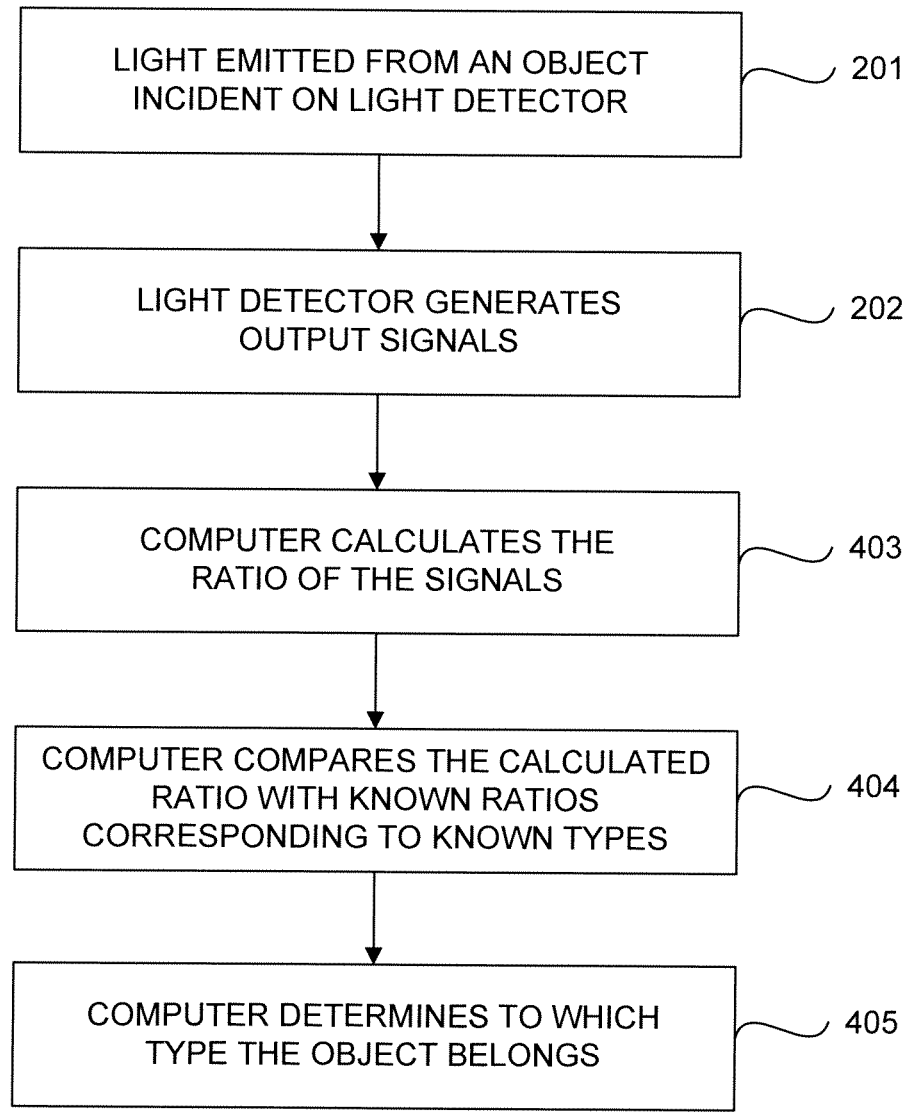
FIG. 11 is a flow chart illustrating a detecting method according to still another embodiment of the invention.

FIG. 11 shows a flow chart of a method for discriminating an object according to still another embodiment of the present invention. In this embodiment, an object may be determined to belong to one of a plurality of known types of object, i.e., Type 1 to Type n. The first two steps of this embodiment may be the same as those in the above-noted embodiment. At step 403, the computer calculates the ratio of J1 and J2. At step 404, the computer 12 compares the calculated ratio with known ratios corresponding to known types of object. At step 405, the computer 12 determines to which type the object belongs based on the comparison result.

In this embodiment, for example, if, among all the known ratios of the known types, the known ratio of Type i (1≤i≤n) is closest to the calculated ratio, then the object may be determined to be a Type i object.

Figure 12:
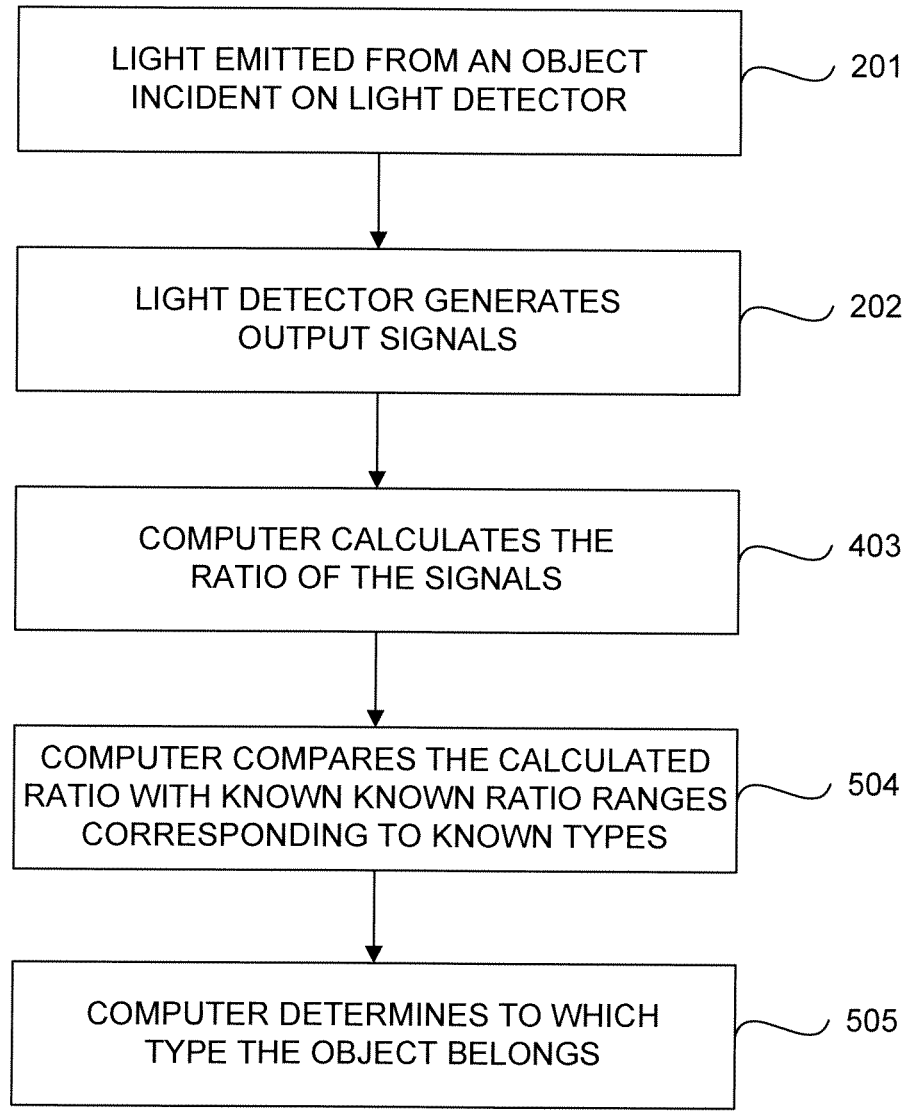
FIG. 12 is a flow chart illustrating a detecting method according to a further embodiment of the invention.

FIG. 12 shows a flow chart of a method for discriminating an object according to a further embodiment of the present invention. In this embodiment, an object may be determined to belong to one of a plurality of known types of object, i.e., Type 1 to Type n. The first three steps of this embodiment may be the same as those in the above-noted embodiment. At step 504, the computer 12 compares the calculated ratio with known ratio ranges corresponding to known types of object. At step 505, the computer 12 determines to which type the object belongs based on the comparison result.

In this embodiment, for example, if the calculated ratio falls within the ratio range corresponding to Type i (1≤i≤n), then the object may be determined to be a Type i object. If the calculated ratio does not fall within any of the ranges, it may be reported that the confidence level is low and that the type of the object being detected may not be determined. For example, assuming Type 1 object has a corresponding ratio range of 0.7<J2/J1<1.2 and Type 2 object has a corresponding ratio range of J2/J1>2, if the calculated ratio for an object being detected is 1, then it may be determined that the object is a Type 1 object. On the other hand, if the calculated ratio for an object being detected is 1.5, then it may be reported that the confidence level is low and that the type of the object may not be determined.

In one embodiment, the ratio of J1 and J2 may be J2/J1. In one embodiment, the ratio of J1 and J2 may be J1/J2. In some embodiments, the ratio of J1 and J2 may be J2/(c×J1) or J1/(c×J2), where "c" is a coefficient.

In some embodiments, after signals are sent to the computer 12, the computer 12 may additionally perform a step of determining whether an object is present in a sample. In some embodiments, the determination may be performed by comparing the sum of all or some of the signals with a threshold value. In some embodiments, for example, if the sum is equal to or larger than the threshold, it may be determined that an object is present. On the other hand, if the sum is smaller than the threshold, it may be determined that an object is absent. In other embodiments, if the sum is smaller than the threshold value, it may be determined that an object is present. If the sum is equal to or larger than the threshold value, it may be determined that an object is absent. In some embodiments, the determination may be performed by comparing the signals directly with a threshold to determine the presence of an object. For example, if any signal is, or a certain number of signals are, equal to or larger than the threshold, it may be determined that an object is present. On the other hand, if all the signals are smaller than the threshold, it may be determined that an object is absent.

In some embodiments, the light detector 11 may comprise three or more optical sensors, each generates an output signal upon the light emitted from an object incident on the light detector 11. In some embodiments, two of the generated output signals may be processed by the computer 12 to discriminate the object. In other embodiments, more or all of the generated output signals may be processed by the computer 12 to discriminate the object.

Figure 13:
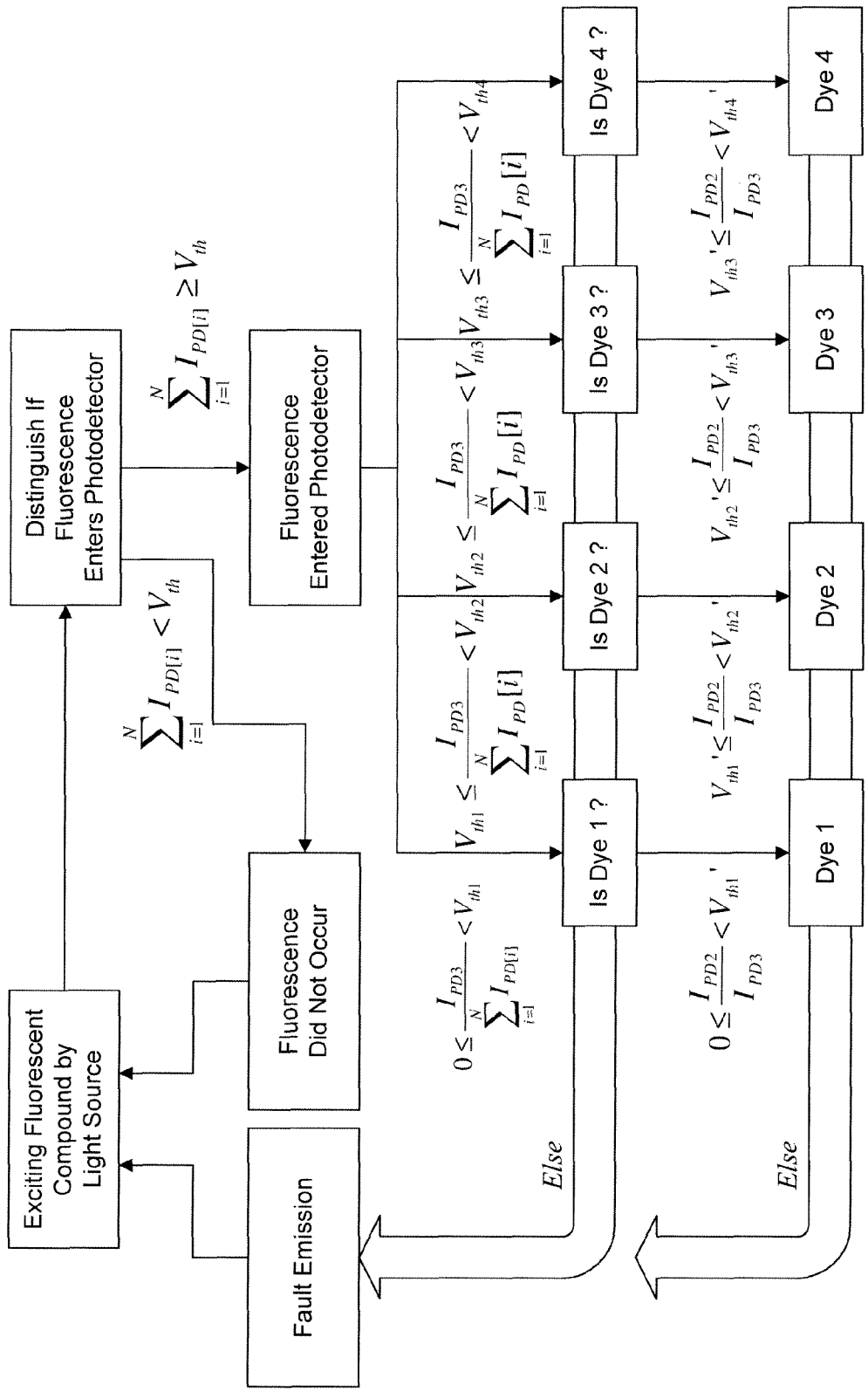
FIG. 13 is a flow chart illustrating a detecting method according to yet another embodiment of the invention.

FIG. 13 shows a flow chart of a method for discriminating an object according to yet another embodiment of the present invention. In this embodiment, the light detector 11 comprises three optical sensors PD1, PD2, and PD3. An object in a sample may be detected and determined to belong to, e.g., one of four types, such as dye 1, dye 2, dye 3, and dye 4. Output signals generated by these three optical sensors are represented by $I_{PD1}$, $I_{PD2}$, and $I_{PD3}$, respectively, and sent to the computer 12 for processing. The method is described below.

First, the sample may be excited using an excitation light source. Optical sensors PD1, PD2, and PD3 may then generate output signals $I_{PD1}$, $I_{PD2}$, and $I_{PD3}$. Upon receiving the output signals, the computer 12 may calculate a sum of these signals. If the sum is smaller than a threshold value $V_{th}$, the computer 12 may generate a report that no fluorescence occurred. Otherwise, the computer may proceed to the next step.

When it is determined that fluorescence did occur and that an object exists, the computer 12 may first perform an original discrimination step. In this step, the computer 12 may calculate a first ratio between $I_{PD3}$ and the sum of all signals, and compare this ratio with a first set of threshold values, e.g., $V_{th1}$, $V_{th2}$, $V_{th3}$, and $V_{th4}$, to determine whether the calculated first ratio falls within any range between 0 and $V_{th1}$, between $V_{th1}$ and $V_{th2}$, between $V_{th2}$ and $V_{th3}$, or between $V_{th3}$ and $V_{th4}$. If, however, the calculated first ratio does not fall in any of the above ranges, the computer 12 may generate a report that a fault emission occurred.

After that, a confirmation step is performed. In the confirmation step, a second ratio between $I_{PD2}$ and $I_{PD3}$ is calculated, and is compared with a second set of threshold values, e.g., $V_{th1}'$, $V_{th2}'$, $V_{th3}'$, and $V_{th4}'$. to determine whether the calculated second ratio falls within any range between 0 and $V_{th1}'$, between $V_{th1}'$ and $V_{th2}'$, between $V_{th2}'$ and $V_{th3}'$, or between $V_{th3}'$ and $V_{th4}'$.

For example, if, in the original discrimination step, the calculated first ratio falls within the range between $V_{th1}$ and $V_{th2}$, it may be determined that the object possibly belongs to the type dye 2. The computer 12 may then proceed to the confirmation step to determine whether the calculated second ratio falls within the range between $V_{th1}'$ and $V_{th2}'$. If yes, it may be determined that the object belongs to the type dye 2. Otherwise, the computer 12 may generate a report that a fault emission occurred.

It is noted that any one of the original discrimination step and the confirmation step described above may be performed individually to discriminate an object. Performing both two steps in one discrimination procedure, however, may improve the accuracy.

Figure 14:
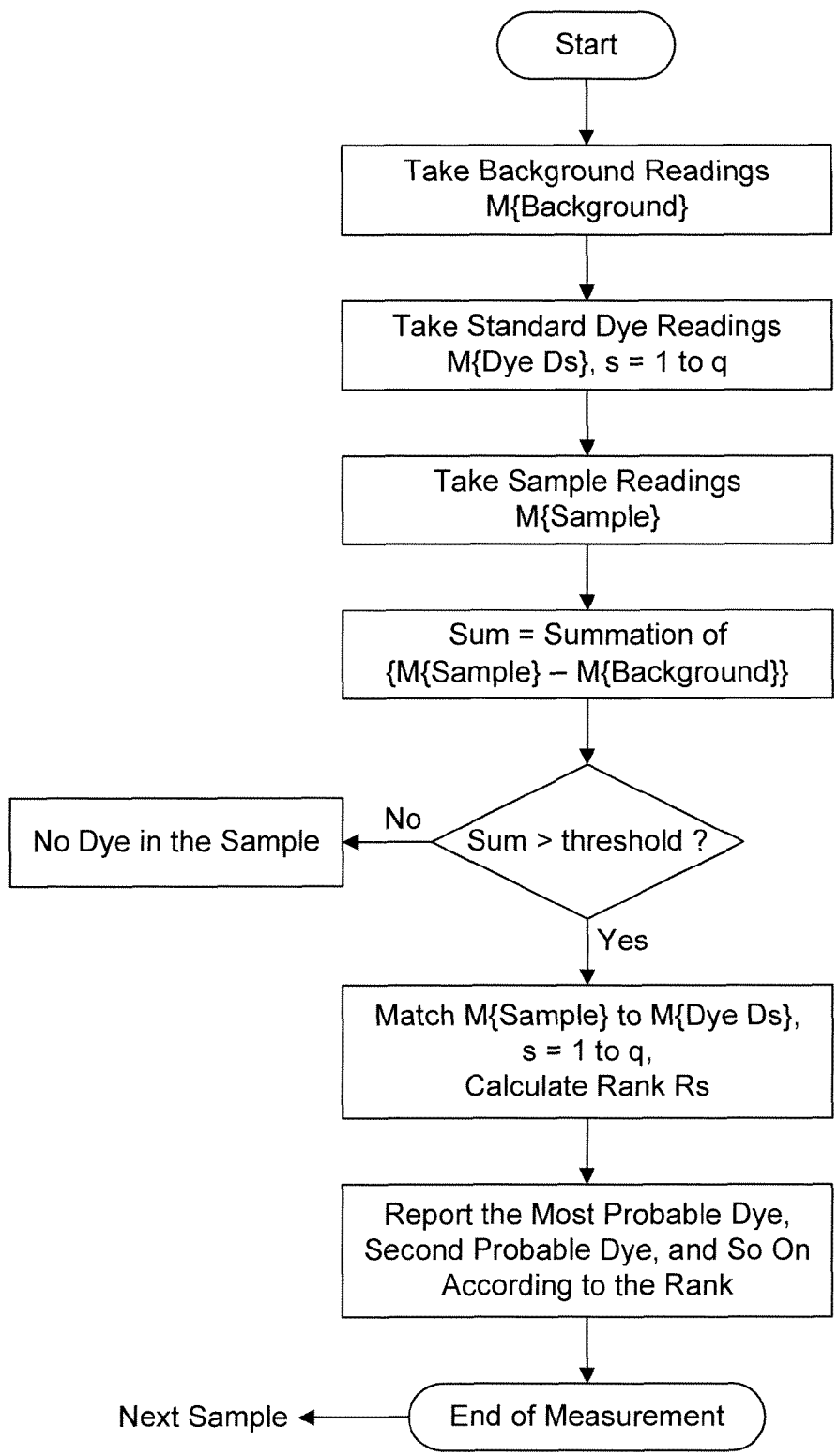
FIG. 14 is a flow chart illustrating a detecting method according to yet a further embodiment of the invention.

FIG. 14 shows a flow chart of a method for discriminating an object according to yet a further embodiment of the present invention. In this embodiment, the light detector 11 comprises a plurality of optical sensors PD1, PD2, . . . PDn, where n is larger than 1 and may be equal to or smaller than 6. Moreover, n may be equal to 3. The apparatus and method of this embodiment may be used to detect and discriminate q different objects, e.g., q different dyes, denoted as D1, D2, . . . Dq.

The excitation light source used in this embodiment may have k different excitation light bands, L1, L2, . . . Lk, where k may be equal to or larger than 1 and equal to or smaller than 3. The excitation light source may turn on and off following a set of instructions, resulting in a set of m different excitation conditions Cj, where $1 \leq j \leq m$. Each excitation condition may be a combination of different excitation light bands. Under the same excitation condition, the output signal generated by a certain optical sensor for different dyes may be different.

The output signal generated at the i-th optical sensor PDi (where $1 \leq i \leq n$) under the j-th excitation condition Cj for a certain dye Ds (where $1 \leq s \leq q$) may be denoted as Ds{J{PDi:Cj}}. Different combinations of PDi and Cj may result in different Ds{J{PDi:Cj}}. Therefore, before using the apparatus to detect and discriminate an unknown dye, by performing calibration reading using different combinations of PDi and Cj at standard environments for a dye Ds, one may obtain a matrix of output signals. This matrix may be unique to a dye, and may be called a standard reading matrix for a dye Ds, M{dye Ds}, as shown below:

| Ds{J{PD1:C1}}, | Ds{J{PD2:C1}}, | . . . | Ds{J{PDn:C1}} |
|---|---|---|---|
| Ds{J{PD1:C2}}, | Ds{J{PD2:C2}}, | . . . | Ds{J{PDn:C2}} |
| . . . | | | |
| Ds{J{PD1:Cm}}, | Ds{J{PD2:Cm}}, | . . . | Ds{J{PDn:Cm}} |

This calibration reading may be repeated for each of the dyes, creating q standard reading matrices M{dye D1}, M{dye D2}, . . . M{dye Dq}.

To minimize the impact of the background, a background reading may also be obtained by recording output signals from the optical sensors when no dye exists, which may result in a background reading matrix M{background}:

| B{J{PD1:C1}}, | B{J{PD2:C1}}, | . . . | B{J{PDn:C1}} |
|---|---|---|---|
| B{J{PD1:C2}}, | B{J{PD2:C2}}, | . . . | B{J{PDn:C2}} |
| . . . | | | |
| B{J{PD1:Cm}}, | B{J{PD2:Cm}}, | . . . | B{J{PDn:Cm}} |

When an unknown sample is applied to the detecting apparatus, output signals generated by the optical sensors at different excitation conditions are measured and a sample reading matrix M{sample} is obtained:

| J{PD1:C1}, | J{PD2:C1}, | . . . | J{PDn:C1} |
|---|---|---|---|
| J{PD1:C2}, | J{PD2:C2}, | . . . | J{PDn:C2} |
| . . . | | | |
| J{PD1:Cm}, | J{PD2:Cm}, | . . . | J{PDn:Cm} |

This sample reading matrix may then be compared with the standard reading matrices to determine which type of dye the sample contains. To minimize the impact of the background on the result, the background reading matrix may be subtracted from both the standard reading matrices and the sample reading matrix before comparison.

The comparison may be carried out by calculating a rank Rs for each type of dye Ds. When calculating Rs, weight factors and statistic methods may be applied. For example, a least squared method or a most likelihood method may be used to find the best match. Weight factors may be applied to each optical sensor or excitation light mode to increase the accuracy of the analysis.

After Rs is calculated, the computer 12 may report the most probable dye, the second probable dye, and so on according to the rank Rs.

Figure 15:
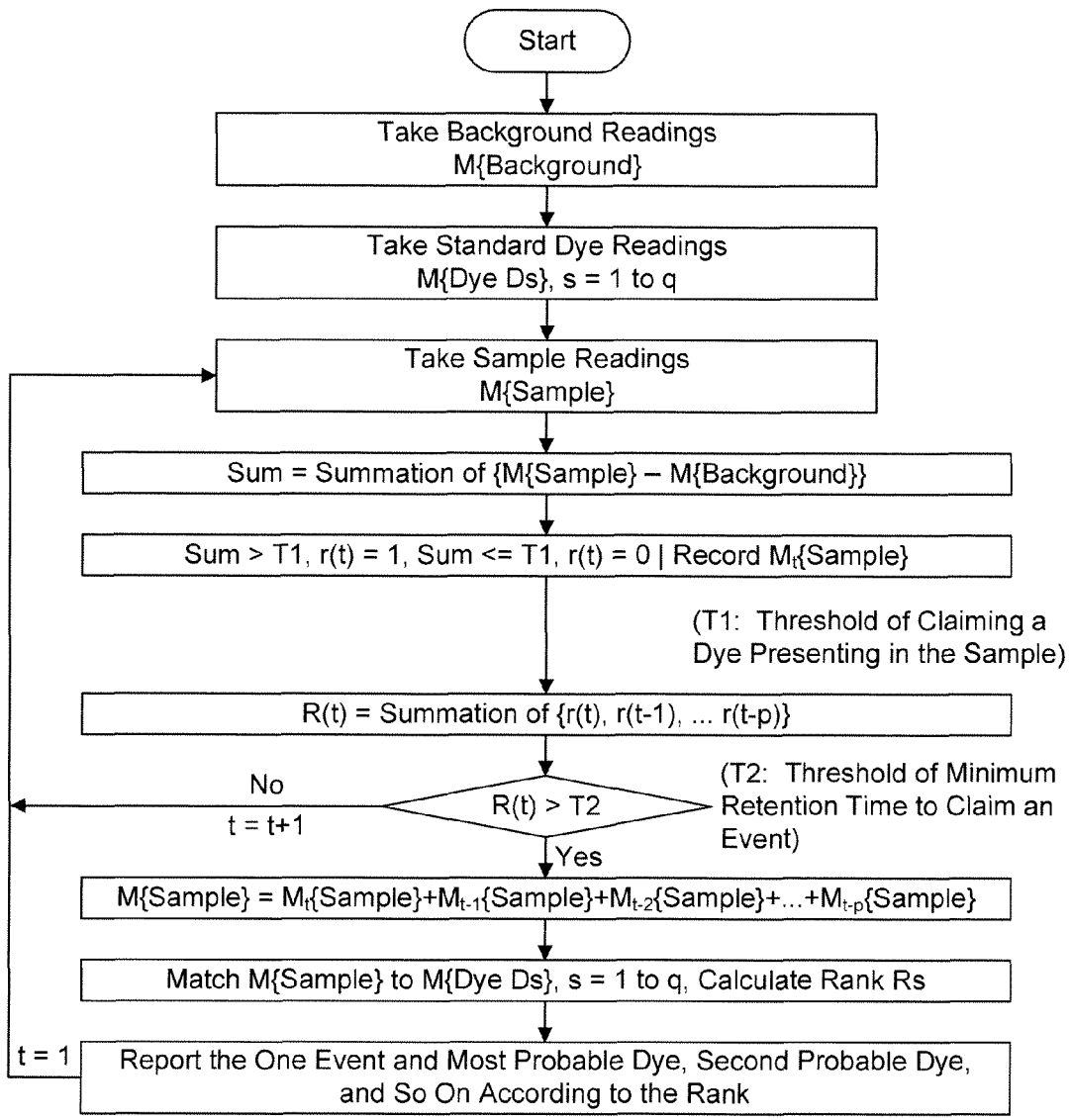
FIG. 15 is a flow chart illustrating a detecting method according to still a further embodiment of the invention.
Figure 16:
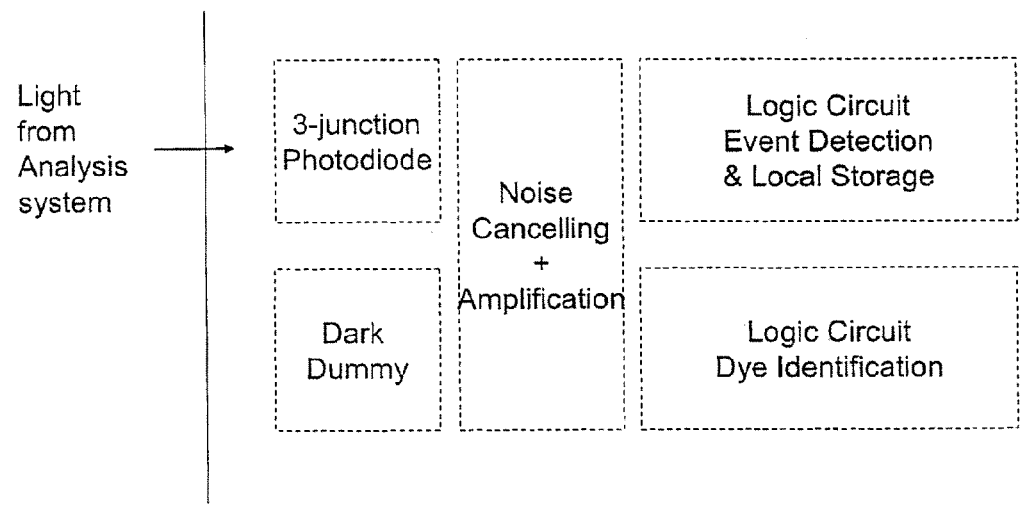
FIG. 16 is a view showing an example detecting apparatus consistent with the present invention.

In the Sequencing by Synthesis method, DNA sequence is determined by identifying the newly added nucleotide to the growing strand. The nucleotide adding process is detected by fluorescent light emitted from the fluorophore attached to the nucleotide. The nucleotide incorporation reaction can be divided into several steps: the nucleotide docking into active site formed by polymerase and template, breaking the phosphate bond, and forming the new bond to the sugar. Some nucleotides just diffuse in and out the active site, with no real incorporation happening. To monitor the incorporation reaction in real time, the detecting apparatus may need to be able to detect a fluorophore coming, time of retention, and type of fluorophore. The reason of measuring retention time is that the diffusing nucleotides may stay for a shorter period of time than those incorporated nucleotides. By setting a retention time threshold, a real incorporation event can be detected. A flow chart of a method according to still a further embodiment of the present invention, which may be used for event detection is shown in FIG. 15. This method is basically similar to that described above, with one more step added to determine whether an event can be claimed. Therefore, detailed description of this method is omitted. FIG. 16 shows a block diagram of one example detecting apparatus which may be used in this embodiment.

In some embodiments, the light detector 11 may comprise two or more optical sensors arranged horizontally. The signals generated by the horizontally arranged optical sensors may be input to the computer 12 and processed in a manner similar to one of the methods disclosed above to determine the presence of an object and/or to discriminate the type of an object.

3. APPLICATIONS

The detecting apparatuses and systems consistent with the present invention, and method of using the same may be applied to, e.g., nucleic acid detection, DNA sequencing, biomarker identification, or flow cytometry. The detecting apparatuses can detect and process low intensity light signal, which makes single molecule object discrimination possible.

In some embodiments of the methods of the present invention, labels are attached to the analyte(s) (i.e., the substance(s) to be detected), the probe(s), such as primers, antibodies, or other reagents that interact with the analyte(s), or other reagent(s), such as nucleotides (including nucleotide analogs). Any label can be used on the analyte or probe which can be useful in the correlation of signal with the amount or presence of analyte.

For example, a wide variety of fluorescent molecules can be utilized in the present invention including small molecules, fluorescent proteins and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein, 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine, ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AFPs-AutoFluorescent Protein-(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (Tetramethyl-RodaminelsoThioCyanate); True Blue; Tru Red; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), also covering a wide spectrum such as Cy3, Cy3B, Cy3.5, Cy5, Cy5.5, Cy7; members of the Oyster dye fluorophores (Denovo Biolabels) such as Oyster-500, -550, -556, 645, 650, 656; members of the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481 XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor series or Quasar series of dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670; quantum dots, such as quantum dots of the EviTags series (Evident Technologies) or quantum dots of the Qdot series (Invitrogen) such as the Qdot 525, Qdot565, Qdot585, Qdot605, Qdot655, Qdot705, Qdot 800; fluorescein; rhodamine; and/or phycoerythrin; or combinations thereof. See, e.g., U.S. Application Publication 2008/0081769.

In some embodiments, at least one bioluminescent or chemiluminescent system is provided which generates light in the presence of an entity such as an analyte, reagent, or reaction product. For example, a bioluminescent or chemiluminescent system can be used to detect pyrophosphate generated in a sequencing by synthesis reaction (discussed in more detail below); to detect the presence of metals such as iron or copper by their catalysis of a light-generating reaction; or to measure the amount of a reagent bound by an analyte, wherein the reagent comprises at least one component of the bio- or chemi-luminescent system.

Examples of bioluminescent systems known in the art include systems comprising at least one luciferase, e.g., firefly luciferases, including *Photinus pyralis* luciferase. A bioluminescent system can be used to detect pyrophosphate, for example, by providing luciferase, ATP sulfurylase, luciferin, and adenosine 5' phosphosulfate, together with the components of the sequencing by synthesis reaction (in which dATP can be substituted with an analog such as dATPαS to avoid nonspecific light due to consumption of dATP by luciferase). When pyrophosphate is generated by a nucleotide incorporation event, ATP sulfurylase produces ATP in an adenosine 5' phosphosulfate dependent manner. The ATP drives conversion of luciferin to oxyluciferin plus light by luciferase. Other bioluminescent systems include systems based on photoproteins such as aequorin, which oxidizes coelenterazine to excited coelenteramide, which emits light.

Examples of chemiluminescent systems include luminol plus hydrogen peroxide, which can undergo a light-emitting reaction in the presence of a metal catalyst or auxiliary oxidant; diphenyl oxalate plus hydrogen peroxide and a suitable dye, which undergoes excitation and light emission in a multistep reaction that produces carbon dioxide (examples of suitable dyes include phenylated anthracene derivatives such as 9,10-diphenylanthracene, 9,10-Bis(phenylethynyl)anthracene, and 1-Chloro-9,10-bis(phenylethynyl)anthracene, and rhodamines such as rhodamine 6G and rhodamine B); singlet oxygen-producing systems such as hydrogen peroxide plus sodium hypochlorite; and systems comprising an enzyme such as horseradish peroxidase, which acts on luminol or other commercially available substrates.

In some embodiments, the methods of the invention comprise forming covalent attachments, such as between reagents or analytes and surfaces or labels. For example, in single molecule sequencing procedures, a nucleic acid molecule or an enzyme such as a polymerase may be attached to a surface such as a glass slide. Such an attachment can allow the acquisition of data over multiple sequencing cycles. In some embodiments, Many methods for forming covalent attachments, such as of reagents to surfaces or labels, are known in the art. Non-covalent attachment methods can also be used. A number of different chemical modifiers can be used to facilitate attachment formation. Examples of chemical modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. Surfaces such as glass slides with such chemically modified surfaces are commercially available for a number of modifications. These can easily be prepared for the rest, using standard methods (Microarray Biochip Technologies, Mark Schena, Editor, March 2000, Biotechniques Books). In some embodiments, attachments are formed between two entities by using an appropriate combination of modifiers (e.g., an electrophilic modifier and a nucleophilic modifier), wherein each entity comprises at least one modifier.

In some embodiments, attachments are formed between two entities by using a chemical modifier present on one of the entities and a naturally occurring moiety, for example, an amine or sulfhydryl, of the other entity. In some embodiments, modifiers that are reactive to amines are used. An advantage of this reaction is that it can be fast and can avoid production of toxic by-products. Examples of such modifiers include NHS-esters, aldehydes, epoxides, acyl halides, and thio-esters. Most proteins, peptides, glycopeptides, etc., have free amine groups, which can react with such modifiers to link them covalently to these modifiers. Nucleic acid probes with internal or terminal amine groups can also be synthesized, and are commercially available (e.g., from IDT or Operon). Thus, biomolecules can be bound (e.g., covalently or non-covalently) to labels, surfaces, or other reagents using similar chemistries.

A number of other multi-functional cross-linking agents can be used to convert the chemical reactivity of one kind of modifier to another. These groups can be bifunctional, tri-functional, tetra-functional, and so on. They can also be homo-functional or hetero-functional. An example of a bi-functional cross-linker is X—Y—Z, where X and Z are two reactive groups, and Y is a connecting linker. Further, if X and Z are the same group, such as NHS-esters, the resulting cross-linker, NHS—Y—NHS, is a homo-bi-functional cross-linker and could connect two entities that each comprise an amine. If X is NHS-ester and Z is a maleimide group, the resulting cross-linker, NHS—Y-maleimide, is a hetero-bi-functional cross-linker and could link an entity comprising an amine with an entity comprising a thio-group. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc.

Other modifier alternatives (such as photo-crosslinking and thermal crosslinking) are known to those skilled in the art. Commercially available technologies include, for example, those from Mosiac Technologies (Waltham, Mass.), EXIQON™ (Vedbaek, Denmark), Schleicher and Schuell (Keene, N. H.), Surmodics™ (St. Paul, Minn.), XENOPORE™ (Hawthorne, N. J.), Pamgene (Netherlands), Eppendorf (Germany), Prolinx (Bothell, Wash.), Spectral Genomics (Houston, Tex.), and COMBIMATRIX™ (Bothell, Wash.).

In some embodiments, surfaces other than glass are provided. For example, metallic surfaces, such as gold, silicon, copper, titanium, and aluminum, metal oxides, such as silicon oxide, titanium oxide, and iron oxide, and plastics, such as polystyrene, and polyethylene, zeolites, and other materials can also be used. In some embodiments, the layers of these materials can be thin, e.g., less than about 100 nm in order to allow the transmission of light.

3.1 Nucleic Acid Detection

A detecting apparatus consistent with the present invention may be used as part of a system for or in methods or processes of molecule detection, e.g., nucleic acid sequencing. This apparatus, and methods or processes utilizing it, are useful for, e.g., analytical and diagnostic applications. These applications may be private, public, commercial, or industrial.

A detecting apparatus consistent with the present invention may be used with a wide variety of sequencing modalities and may be suitable for sequencing single molecules. Additionally, the detecting apparatus consistent with the present invention have simplified design, assembly, and production relative to existing biochip devices. For example, the nucleic acids to be sequenced may be affixed to random linker sites on the array of the system, avoiding the use of time consuming and expensive robotics to deposit or synthesize nucleic acids at predetermined locations.

A detecting apparatus consistent with the present invention may be used as part of a system for or in methods and processes of biomolecule detection, including nucleic acid hybridization or sequencing for, e.g., whole genome sequencing, transcriptional profiling, comparative transcriptional profiling, or gene identification. Biomolecule detection can also include detection and/or measurement of binding interactions, e.g., protein/protein, antibody/antigen, receptor/ligand, and nucleic acid/protein. These applications are useful for analytical or diagnostic processes and methods.

Nucleic acids suitable for detection on the apparatus provided by the invention may, in some embodiments, be part of a linking molecule, which affixes a molecule suitable for assaying binding interactions, e.g., proteins, other nucleic acids, carbohydrate moieties, or small molecules to a linker site on a device provided by the invention. The linking molecule may, in some embodiments, further comprise a capture molecule, which binds to the molecule being assayed for binding interactions. The nucleic acid in a linking molecule serves as an identifying tag for the capture molecule of the linking molecule by, e.g., direct sequencing or hybridization.

The methods provided by the invention may comprise a step of affixing a molecule to be detected to an address array of a detecting system provided by the invention. In some embodiments, the address array may include a blind sheet having a plurality of pinholes, and linker sites may be formed in or around the pinholes. Thus, a detecting system consistent with the present invention may simultaneously read millions of nucleic acid segments. If each segment is, for example, 1000 bases long, a single device could obtain billions of bits of sequence information, making, e.g., whole genome sequencing and resequencing possible.

3.1.1 Molecules to be Detected

Nucleic acids suitable for detection by the methods provided by the present invention may include any nucleic acid, including, for example, DNA, RNA, or PNA (peptide nucleic acid), and may contain any sequence—both known and unknown, including naturally occurring or artificial sequences. The nucleic acid may be naturally derived, recombinantly produced, or chemically synthesized. The nucleic acid may comprise naturally-occurring nucleotides, nucleotide analogs not existing in nature, or modified nucleotides. The length of the nucleic acid to be detected may vary based on the actual application. In some embodiments, the nucleic acid may include at least 10, 20, 50, 100, 200, 500, 1000, 2000, 5000, 10000, 20000 bases, or more. In some embodiments, the nucleic acid may be from 10 to 20, from 10 to 50, from 10 to 100, from 50 to 100, from 50 to 500, from 50 to 1000, from 50 to 5000, from 500 to 2000, from 500 to 5000, or from 1000 to 5000 bases.

A nucleic acid may be single-stranded for detection. Single stranded nucleic acid templates may be derived from a double stranded molecule by means known in the art including, for example, heating or alkali or other chemical treatment. Single stranded nucleic acid templates may also be produced by, e.g., chemical or in vitro synthesis.

In some embodiments, the nucleic acid to be detected may be attached to a linker site at its 5' or 3' end. In some embodiments, the nucleic acid may further comprise one or more end link primers coupled to the 5' end, the 3' end, or both the 5' end and the 3' end of the nucleic acid. In particular embodiments, an end link primer may be affixed to the 3' end of the nucleic acid. End link primers may be used both to affix the nucleic acid to be detected to linker sites on the device and provide a complementary sequence for one or more detecting primers, e.g., a sequencing primer.

3.1.1.1 End Link Primer

End link primers are short nucleic acid molecules usually composed of less than 100 nucleotides. In some embodiments, the end link primer may be at least 5, 10, 15, 20, 25, 30, 50, 75, 90 nucleotides, or more, in length. In certain embodiments, end link primers may be from 8 to 25, from 10 to 20, from 10 to 30, or from 10 to 50 nucleotides in length. In some embodiments, the end link primers may be unbranched, however, in other embodiments, they may be branched.

The end link primer may be used to attach the nucleic acid to be detected to a linker site on the address array. In some embodiments, the end link primer may link the nucleic acid to the array surface directly, e.g., by covalent linkage (e.g., ester or thiol linkage) or non-covalent linkage, e.g., antigen/antibody or biotin/avidin binding. In some embodiments, the end link primer may link the nucleic acid to the array surface indirectly, e.g., by binding an intermediate molecule, e.g., a polymerase. Accordingly, the end link primer may contain modified nucleotides or be otherwise modified to facilitate attachment to a linker site by means known in the art, e.g., disulfide, thioester, amide, phosphodiester, or ester linkages; or by, e.g., antibody/antigen or biotin/avidin binding, e.g., the end link primer may contain a nucleotide comprising an antigen moiety or a biotinylated nucleotide. In particular embodiments, a modified nucleotide may be on the 3' end of an end link primer. In some embodiments, the 5' end of an end link primer may contain a modified nucleotide.

The end link primer may also serve as a complement to one or more primers used to detect the nucleic acid, e.g., a sequencing primer. In some embodiments, the primer may be used to detect the nucleic acid by hybridization, e.g., the primer may contain a detectable label, e.g., a fluorescent label. In some embodiments, the 5' end of the end link primer may comprise a sequence complementary to a sequencing primer. In some embodiments, the end link primer sequence that is complementary to the sequencing primer may be oriented so that the 3' end of the sequencing primer may be immediately adjacent to the first nucleotide in the nucleic acid to be sequenced.

In some embodiments, end link primers may be added to ends of the nucleic acid to be detected by a ligase, for example, a DNA ligase. In some embodiments, the end link primer and nucleic acid to be detected may be both single stranded before the ligation. In other embodiments, both may be double stranded. In still other embodiments, one may be single stranded and the other may be double stranded. Ligation is well known in the art. For example, in the polony sequencing method, Shendure et al. (*Science*, 309:1728-1732 (2005)) ligated a T30 end link primer (32 bp) to a sample DNA segment with the New England Biolabs' (NEB) Quick Ligation kit. There, the ligation reaction solution included 0.26 pMole of DNA, 0.8 pMole of T30 end link primer, 4.0 µl T4 DNA Ligase, in 1× Quick Ligation Buffer. After mixing, the reaction solution was incubated for about 10 minutes at room temperature, and then placed on ice. The ligation reaction was stopped by heating the samples to 65° C. for 10 minutes.

In other embodiments, the end link primer may be synthesized on the nucleic acid to be detected. For example, the end link primer may be a homopolymer added by, e.g., terminal transferase. For example, Harris et al., (*Science* 320:106-109 (2008)) added a poly A tail to DNA templates, which served as the complement to a poly T sequencing primer in the single molecule sequencing of a viral genome.

3.1.1.2 Sequencing Primer

A sequencing primer is a single-stranded oligonucleotide complementary to a segment of the nucleic acid to be detected or its associated end link primer. In some embodiments, the sequencing primer may be at least 8, 10, 15, 20, 25, 30, 35, 40, 45, 50 nucleotides, or more in length. In particular embodiments, the sequencing primer may be from 8 to 25, from 10 to 20, from 10 to 30, or from 10 to 50 nucleotides in length. The sequencing primer may be made up of any type of nucleotide, including naturally-occurring nucleotides, nucleotide analogs not existing in nature, or modified nucleotides. In certain embodiments, the 5'-end of a sequencing primer may be modified to facilitate binding to a linker site on the address array after the sequencing primer hybridizes with a nucleic acid to be sequenced, including one or more end link molecules.

In some embodiments, a sequencing primer may contain modified nucleotides, e.g., locked nucleic acids (LNAs; modified ribonucleotides, which provide enhanced base stacking interactions in a polynucleic acid). As an illustration of the utility of LNAs, Levin et al. (Nucleic Acid Research 34(20):142 (2006)) showed that a LNA-containing primer had improved specificity and exhibited stronger binding relative to the corresponding unlocked primer. Three variants of the MCP1 primer (5'-cttaaattttcttgaat-3') containing 3 LNA nucleotides (in caps) at different positions in the primer were made: MCP1-LNA-3'(5'-cttaaattttCtTgaAt-3'); MCP1-LNA-5'(5'-CtTaAattttcttgaat-3'); and MCP1-LNA-even (5'-ctTaaatTttctTgaat-3'). All LNA-substituted primers had enhanced Tm, while the MCP1-LNA-5' primer exhibited particularly enhanced sequencing accuracy (Phred Q30 counts). Accordingly, in particular embodiments, the sequencing primer may contain at least one locked nucleotide in its 5' region, i.e., the 5' half, third, or quarter of the sequencing primer.

Sequencing primers and single stranded sample nucleic acids (i.e., a nucleic acid to be detected including at least one end link primer) may be hybridized before being applied to a detecting apparatus consistent with the present invention. The sequencing primer and sample nucleic acid may be hybridized by mixing the sample nucleic acid with a molar excess of sequencing primer in a salt-containing solution, such as 5×SSC (or 5×SSPE), 0.1% Tween 20 (or 0.1% SDS), and 0.1% BSA buffer. The mixture may be heated to 65° C. for at least 5 minutes and slowly cooled to room temperature, to allow primer/template annealing. Residual primers may be eliminated by appropriate means including, e.g., a molecular sieve.

Primers, including both end link and sequencing primers, may be designed by appropriate means, including visual inspection of the sequence or computer-assisted primer design. Numerous software packages are available to assist in the primer design, including DNAStar™ (DNAStar, Inc., Madison, Wis.), OLIGO 4.0 (National Biosciences, Inc.), Vector NTI® (Invitrogen), Primer Premier 5 (Premierbiosoft), and Primer3 (Whitehead Institute for Biomedical Research, Cambridge, Mass.). Primers may be designed taking into account, for example, the molecule to be sequenced, specificity, length, desired melting temperature, secondary structure, primer dimers, GC content, pH and ionic strength of the buffer solution, and the enzyme used (i.e., polymerase or ligase). See, e.g., Joseph Sambrook and David Russell, *Molecular Cloning: A Laboratory Manual* Cold Spring Harbor Laboratory Press; 3rd edition (2001).

3.1.1.3 Bonding to the Array Surface

After the sequencing primer and nucleic acid to be sequenced, including one or more end link primers, are annealed, this complex may be prepared in a suitable buffer, applied to the surface of an address array, and allowed to bind. In some embodiments the sample nucleic acid (nucleic acid to be detected and one or more end link primers) may be affixed to linker sites and sequencing or detecting primers may be later applied. In other embodiments, the complex may be hybridized before being applied to a device. Linker sites where only one sample nucleic acid is bound are known as effective addresses. In certain embodiments, the complex may be applied to the detecting system and the sample nucleic acids affixed to random linker sites on the address array. In other embodiments, sample nucleic acids may be applied to predetermined linker sites on the address array by appropriate means, including, e.g., by robotics or liquid handling systems.

Appropriate means for affixing nucleic acids to a solid support are well known in the art. In some embodiments, the sample nucleic acid may be affixed directly to a linker site by covalent linkage, e.g., disulfide, thioester, amide, phosphodiester, or ester linkages; or by non-covalent linkage, e.g., antibody/antigen or biotin/avidin binding. In some embodiments, the sample nucleic acid may be affixed to a linker site by an intervening molecule. In some embodiments, the intervening molecule may be a polymerase, e.g., a DNA polymerase.

As an illustrative example of direct, covalent attachment of a nucleic acid, Adeesi et al. (Nucleic Acid Research, 28:87 (2000)) modified the 5' end of a primer to include a SH functional group. According to the method of Adeesi et al., a nucleic acid may be prepared in 50 µM phosphate buffered saline ("PBS") (NaPi: 0.1 MNaH$_2$PO$_4$ pH 6.5, 0.1 M NaCl). About 1-5 µl of primer solution may then be applied to a surface of a silanised glass slide and incubated in a humidity control box at room temperature for about 5 hours to bond the primer to the chip surface. After the binding reaction is completed, the PBS solution is vibration washed twice at room temperature for 5 minutes each to remove un-bonded DNA. After cleaning, 10 mM β-mercaptoethanol is added to a PBS solution and used to rinse the address array surface under room temperature, to deactivate the thiol group of un-bonded DNA. Next, the array surface is washed, e.g., once with 5×SSC 0.1% Tween and once with 5×SSC buffer solution. Accordingly, in some embodiments, the method used by Adeesi et al. can be used in the methods provided by the invention to affix the sample nucleic acid complex to a linker site, e.g., via the 5' end of a sequencing primer or the sample nucleic acid.

In an alternative embodiment, the sample nucleic acid may comprise, e.g., a biotinylated nucleotide, and binds to avidin on the linker site surface. In another embodiment, the sample nucleic acid may comprise an antigenic moiety, e.g., BrdU or digoxigenin, that is bound by an antibody (or fragment thereof) on the linker site. By "antibody" it is to be understood that this term includes fragments of immunoglobin molecules, including, for example, one or more CDR domains; or variable heavy or variable light fragments. Antibodies may be naturally occurring, recombinant, or synthetic. Antibodies may also include, e.g., polyclonal and monoclonal variants. In some embodiments the antibodies may bind their antigen(s) with association constants of at least $10^6$, $10^7$, $10^8$, $10^9$ M, or higher. The structure, function, and production of antibodies are well known in the art. See, for example, Gary Howard and Matthew Kasser, *Making and Using Antibodies: A Practical Handbook* CRC Press; 1$^{st}$ edition (2006).

In yet another embodiment, the sample nucleic acid may be affixed to the linker site by a polymerase, e.g., DNA polymerase. The skilled artisan will appreciate, that to retain enzyme function available information, such as the primary, secondary, and tertiary structures of the enzyme, should be taken into consideration. For example, the structures of Taq and Phi29 polymerases are known in the art, see: Kim et al., *Nature,* 376:612-616 (1995) and Kamtekar et al., *Mol. Cell,* 16:609-618 (2004), respectively. Means for fixing a polymerase to a surface, while retaining activity are known in the art and are described in, e.g., U.S. Patent Application Publication No. 2008/0199932, published Aug. 21, 2008 and Korlach et al. *PNAS* 105:1176-1181 (2008).

In some embodiments, an aldehyde-modified surface of a linker site is treated with aldehyde-containing silane reagent. The aldehydes readily react with primary amines on the proteins to form a Schiff's base linkage. Because many proteins display lysines on their surfaces in addition to the generally more reactive α-amine at the NH$_2$-terminus, they may attach to the slide in a variety of orientations, permitting different sides of the protein to interact with other proteins or small molecules in solution. In another embodiment, a photoNHS (a N-hydroxy succimido carboxylate molecule linked to an azidonitrobenzene molecule with a carbon chain linker) may attach to an amine-modified surface on the device by UV photoactivation. In these embodiments, UV light excites the azidonitrobenzene moiety to produce highly reactive nitrene, by eliminating nitrogen. Nitrene readily reacts with NH$_2$ on the surface of the device and forms a hydrazine bond. The other end of the linker is NHS carboxylate, which react with lysines on the surface of polymerase to produce an amide covalent bond. In another embodiment, an NHS carboxylate moiety may be reacted with primary amine on the surface of the device under buffered conditions. UV light may be used to activate an azidonitrobenzene moiety and form a highly reactive nitrene as an electron deficient group and readily react with primary amine of lysine residues on the polymerase.

3.1.2 Sequencing Modalities

The detecting apparatuses and methods provided by the present invention may be used to detect and sequence nucleic acids by means known in the art, as reviewed in, e.g., U.S. Pat. No. 6,946,249 and Shendure et al., *Nat. Rev. Genet.* 5:335-44 (2004). The sequence modalities can be chosen from single molecule sequencing methods known in the art. In some embodiments, the sequencing methods may rely on the specificity of either a DNA polymerase or DNA ligase and may include, e.g., base extension sequencing (single base stepwise extensions), multi-base sequencing by synthesis (including, e.g., sequencing with terminally-labeled nucleotides), and wobble sequencing, which is ligation-based. The methods typically involve providing a sample nucleic acid, which may include at least one end link primer. The nucleic acid can be affixed to a substrate (either directly or indirectly), e.g., at a linker site. The nucleic acid may be provided in single stranded form or may be rendered single stranded, e.g., by chemical or thermal denaturation. Sequencing may be then initiated at a sequencing primer (ligase-based sequencing commonly refers to anchor primers, which serve the analogous purpose to sequencing primers).

For single molecule sequencing modalities, the present invention can offer the advantage of being able to resequence single molecules. For example, after completion of a sequencing read, the sequencing primer and extended nucleotides may be stripped from the sample nucleic acid, the device is washed, and the sequencing is repeated. In various embodiments, the resequencing may be done by the same or different methods. By resequencing the same molecule, sequencing errors are expected to fall as the power of the number of sequencing reads. For example, if per base error rates for a single read are $10^{-3}$, then after two reads, this falls to $(10^{-3})^2$, i.e., $10^{-6}$. This is particularly advantageous for single molecule sequencing since the modified nucleotides used for sequencing can lose their labels or blocking groups resulting in, e.g., spurious deletions.

In general, in single molecule sequencing, at least one nucleic acid molecule to be sequenced is affixed to a substrate and contacted with a primer. The primer is modified, e.g., by performing at least one enzyme-catalyzed polymerization or ligation reaction. The at least one reaction leads to emission of light correlated to the identity of at least one base comprised by the nucleic acid. "Leading to" emission of light is understood to mean that the at least one reaction causes at least one condition under which light emission correlated to the identity of at least one base comprised by the nucleic acid occurs; this occurrence may be via interaction with excitatory light, a chemi- or bio-luminescent system, etc. The at least one condition can be, for example, incorporation of a fluorophore into the product of the at least one reaction, or the release of pyrophosphate. Thus, light may be generated with or without external excitation. For example, single molecule sequencing can be performed with reversible terminator base analogs comprising a covalently-linked detectable label, e.g., a fluorescent label, and a blocking group to prevent any secondary extension, wherein the analog is excited and detected after it has been added to the primer, and the label and blocking group are removed after addition to allow another round of extension. Alternatively, a product of an extension step, such as a pyrophosphate, can be detected without external excitation by providing a chemi- or bio-luminescent detection system which emits light in a pyrophosphate-dependent manner. These and other modalities are discussed in more detail below.

The light emitted is correlated to the identity of at least one base comprised by the nucleic acid. In some embodiments, the correlation can be temporal; e.g., the time of emission of the light indicates the identity of the at least one base, such as is the case when different base analogs are provided for use in a polymerization reaction at different times. In some embodiments, the correlation can be spectral; e.g., the spectrum of the emitted light indicates the identity of the at least one base, such as is the case when different base analogs that comprise different fluorophores are provided for use in a polymerization reaction.

In some embodiments, single molecule nucleic acid sequencing comprises multiple sequencing cycles. A sequencing cycle is understood to mean the events that lead to an emission of light correlated to the identity of at least one base that would be repeated in order to identify at least a second base comprised by the nucleic acid after a first base has been identified. Thus, in methods according to the invention that comprise single molecule nucleic acid sequencing, the single molecule nucleic acid sequencing can comprise at least a given number of sequencing cycles that lead to at least the given number of emissions of light correlated collectively to the identity of at least the given number of bases comprised by the nucleic acid, and the method comprises identifying at least the given number of bases comprised by the nucleic acid. In some embodiments, the given number may be, for example, 2, 3, 4, 5, 10, 20, 50, 100, 200, or 500.

Sequencing methods can comprise determining the identity of one or more bases comprised by a nucleic acid. In some embodiments of methods according to the invention, in which performing single molecule nucleic acid sequencing leads to emission of light that is detected with at least one light detector comprising at least a first optical sensor and a second optical sensor, and output signal from the at least two optical sensors is processed, the identity of at least one base comprised by a nucleic acid can be determined by comparing at least one result of the processing with at least one known result corresponding to at least one known type.

For example, a result of the processing can indicate a time at which a reaction occurred; when light emitted is temporally correlated to the identity of at least one base comprised by the nucleic acid, said time can be used to identify at least one base comprised by the nucleic acid.

In another example, a result of the processing can be a determination of which fluorophore was incorporated into the product of a reaction; when light emitted is spectrally correlated to the identity of at least one base comprised by the nucleic acid, said determination can be used to identify at least one base comprised by the nucleic acid.

3.1.2.1 Base Extension Sequencing: Stepwise Extension

In some embodiments, a detecting apparatus provided by the invention may be used to detect light generated during base extension sequencing. In some embodiments, base extension sequencing begins by attaching a partial duplex sample nucleic acid comprising a single stranded nucleic acid to be sequenced, an end link primer associated with the 3' end of nucleic acid to be sequenced, and a sequencing primer annealed thereto, to a linker site. In some embodiments, polymerase and modified nucleotides may be then applied to the light detection apparatus in a suitable buffer. In some embodiments, the sample nucleic acid complex may be affixed to the linker site by a polymerase at a linker site. In some embodiments, the nucleotides may include a covalently-linked detectable label, e.g., a fluorescent label, and a blocking group to prevent any secondary extension. Accordingly, the sequencing pauses after the addition of a single nucleotide to the 3' end of sequencing primer.

In a first step of one embodiment of a base extension sequencing reaction, a nucleotide with a fluorescent blocking group may be added by a DNA polymerase to the 3' end of sequencing primer. In some embodiments, the fluorescent label may act as the blocking group. In other embodiments, they may be separate moieties. A single nucleotide may be incorporated at the 3' end of sequencing primer and is identified by its label by the corresponding light detector. The fluorescent label and blocking group are then removed, e.g., by chemical or enzymatic lysis, to permit additional cycles of base extension. In certain embodiments, the label and blocking groups may be removed simultaneously or sequentially and in any order. By compiling the order of the bases added, the sequence of the sample nucleic acid may be deduced in the 3' to 5' direction, one base at a time.

Generally, there are two ways to recognize the nucleotide added during stepwise extension. In the first case, the four nucleotides may all have the same detectable label, but are added one at a time, in a predetermined order. The identity of the extended nucleotide may be determined by the order that the nucleotide is added in the extension reaction. In the second mode for recognizing the base integrated during extension, four different nucleotides may be added at the same time and each is coupled with a distinct detectable label. In different embodiments, the excitation or emission spectra and/or intensity of the labels may differ. The identity of the nucleotide added in the extension may be determined by the intensity and/or wavelength (i.e., excitation or emission spectra) of the detected label.

3.1.2.2 Sequencing by Synthesis: Multi-Step Extension

In some embodiments, sequencing by synthesis may proceed with multiple uninterrupted extensions, e.g., without the use of blocking groups. In these embodiments, the polymerization reaction may be monitored by detecting the release of the pyrophosphate after nucleoside triphosphate hydrolysis, i.e., the release of the $\beta$ and $\gamma$ phosphate complex. This complex may be detected directly, for example, by a fluorescent moiety on the complex, or indirectly, for example, by coupling the pyrophosphate to a chemi- or bio-luminescent detection system, as discussed above.

In some embodiments, the sample nucleic acid may be sequenced essentially continuously by using terminal-phosphate-labeled nucleotides. Exemplary embodiments of terminal-phosphate-labeled nucleotides and methods of their use are described in, e.g., U.S. Pat. No. 7,361,466 and U.S. Patent Publication No. 2007/0141598, published Jun. 21, 2007. Briefly, the nucleotides may be applied to the system provided by the invention and, when hydrolyzed during the polymerization, the labeled pyrophosphate may be detected by a corresponding light detector. In some embodiments, all four nucleotides may comprise distinct labels and be added simultaneously. In some embodiments, the nucleotides may comprise indistinguishable, e.g., identical, labels and be added sequentially in a predetermined order. Sequential, cyclical addition of nucleotides with indistinguishable labels still permits multiple, uninterrupted polymerization steps, e.g., in homopolymer sequences.

3.1.2.3 Ligase-Based Sequencing

In other embodiments, a sample nucleic acid may be sequenced on the apparatus provided by the invention by ligase-based sequencing. Ligase-based sequencing methods are disclosed in, for example, U.S. Pat. No. 5,750,341, PCT publication WO 06/073504, and Shendure et al. *Science*, 309:1728-1732 (2005). In the method of Shendure et al., for example, an unknown single-stranded DNA sample may be flanked by two end link primers and immobilized on a solid support. A particular position in the unknown sequence (e.g., the $n^{th}$ base proximal to a particular end link primer) can be interrogated by annealing a so-called anchor primer (which is analogous to a sequencing primer) to one of the end link primers and then applying a pool of 4 degenerate nonamers to the mixture. The four nonamers all have distinct fluorescent labels and are degenerate at all positions except for the query position, where each nonamer interrogates with a distinct base—A, C, G, or T. The sample is washed, fluorescently scanned, and the query base is identified. The anchor primer and ligated nonamer are then stripped from the sample nucleic acid, the device is washed, and the process is repeated, querying a different position. Advantageously, this method is non-progressive, i.e., bases need not be queried in order. Thus, errors are not cumulative. Additionally, this method can query nucleotides from either the 5' or 3' direction, i.e., does not require canonical 5'→3' DNA synthesis. A total of about 13 bases of a sample nucleic acid can typically be sequenced by this method.

3.1.2.4 Third-Generation Sequencing

In some embodiments, a sample nucleic acid may be sequenced on the apparatus provided by the invention using third-generation sequencing. In third-generation sequencing, a slide with an aluminum coating with many small (~50 nm) holes is used as a zero mode waveguide (see, e.g., Levene et al., *Science* 299, 682-686 (2003)). The aluminum surface is protected from attachment of DNA polymerase by polyphosphonate chemistry, e.g., polyvinylphosphonate chemistry (see, e.g., Korlach et al., *Proc Natl Acad Sci USA* 105, 1176-1181 (2008)). This results in preferential attachment of the DNA polymerase molecules to the exposed silica in the holes of the aluminum coating. This setup allows evanescent wave phenomena to be used to reduce fluorescence background, allowing the use of higher concentrations of fluorescently labeled dNTPs. The fluorophore is attached to the terminal phosphate of the dNTPs, such that fluorescence is released upon incorporation of the dNTP, but the fluorophore does not remain attached to the newly incorporated nucleotide, meaning that the complex is immediately ready for another round of incorporation. By this method, incorporation of dNTPs into an individual primer-template complexes present in the holes of the aluminum coating can be detected. See, e.g., Eid et al., *Science* 323, 133-138 (2009). Use of the detecting system consistent with the present invention may provide high sensitivity, allowing more efficient detection of incorporated dNTPs, resulting in relatively low error rates and/or longer reads of interpretable sequence data.

3.1.3 Additional Applications

A detecting system consistent with the present invention may simultaneously detect millions of nucleic acid segments. If each segment is, for example, 1000 bases long, a single device could obtain upwards of billions of base sequences at once. Discussed below are additional applications of the apparatuses and methods provided herein.

3.1.3.1 Whole Genome Sequencing

A detecting system consistent with the present invention may be used to perform whole or partial genome sequencing of, e.g., a virus, bacterium, fungi, eukaryote, or vertebrate, e.g., a mammal, e.g., a human.

Genomic DNA may be sheared into fragments of at least 20, 50, 100, 200, 300, 500, 800, 1200, 1500 nucleotides, or longer, for sequencing. In some embodiments, the sheared genomic DNA may be from 20 to 50, from 20 to 100, from 20 to 500, from 20 to 1000, from 500 to 1200, or from 500 to 1500 nucleotides long. In some embodiments, the nucleic acids to be sequenced, along with associated end link primers, may be made single stranded, annealed to a sequencing primer, and applied to a system provided by the invention for sequencing as described above.

3.1.3.2 Gene Expression Profiling

In other embodiments, a detecting system consistent with the present invention may be used to sequence cDNA for gene expression profiling. For example, mRNA levels may be quantified by measuring the relative frequency that a particular sequence is detected on a device. Several million cDNA molecules may be sequenced in parallel on a device provided by the invention. If a cell contains, on average, 350,000 mRNA molecules, a transcript present at even one copy per cell is expected to be sequenced approximately three times in one million sequencing reactions. Accordingly, the devices provided by the invention are suitable for single molecule sequencing with single copy number sensitivity.

cDNA synthesis is well known in the art and typically includes total RNA extraction with optional enrichment of mRNA. cDNA is produced from mRNA by steps including, for example: reverse transcription, for first strand synthesis; RNAse treatment, to remove residual RNA; random hexamer priming of the first strand, and second strand synthesis by DNA polymerase. The resultant cDNA is suitable for sequencing on the devices provided by the invention. Methods of isolating and preparing both DNA and RNA are well known in the art. See, for example, Joseph Sambrook and David Russell, *Molecular Cloning: A Laboratory Manual* Cold Spring Harbor Laboratory Press; 3rd edition (2001).

In some embodiments, cDNA may be ligated with adapter poly nucleic acids, the adapters may be processed with specialized restriction enzymes, and finally, the processed nucleic acids bind to complementary oligonucleotides affixed at linker sites of an apparatus provided by the invention. In particular embodiments, the adapter molecules may be end link primers.

In some embodiments consistent with the present invention, the poly-A tail of an mRNA may serve as a suitable end link primer, which is complementary to a poly T sequencing primer.

3.1.3.3 Detecting and/or Measuring Binding Interactions

In other embodiments, a detecting apparatus may be used to detect various binding interactions including, e.g., DNA/DNA, RNA/RNA, or DNA/RNA base pairings, nucleic acid/protein interactions, antigen/antibody, receptor/ligand binding, and enzyme/substrate binding. In general, a sample molecule may be affixed to a linking molecule that comprises an identifying nucleic acid tag (ID). In some embodiments, the linking molecule may further comprise a capture molecule that binds the sample molecule. The linking molecule may also comprise a means for binding to a linker site; e.g., a moiety to facilitate covalent chemical linkage, such as disulfide, thioester, amide, phosphodiester, or ester linkages; or by non-covalent linkage, e.g., antibody/antigen or biotin/avidin binding. In some embodiments, a linking molecule may be affixed to the array by the ID tag.

A sample molecule may be applied to a system consistent with the present invention and affixed to a random linker site by its linker molecule, e.g., by binding a capture molecule located on the linking molecule. In some embodiments, the sample molecule and linker molecules may be mixed, allowed to bind, and then applied to a device provided by the invention. In some embodiments, the linker molecule may be first applied to the device, allowed to affix to a linker site, and then the sample molecule may be applied. Next, the ID may be detected (e.g., by hybridization or sequencing) by the methods consistent with the invention to identify the associated sample molecule. A plurality of sample molecule species may be affixed to the same array and may be distinguished by their label while their binding interactions may be characterized using the unique IDs of the capture molecule it binds to. Thus, in some embodiments, a method of detecting a labeled sample molecule may comprise the steps of linking a sample molecule to a linker site of a system consistent with the present invention by a linker molecule comprising a nucleic acid tag (ID), performing nucleic acid sequencing of the ID, and detecting the labeled sample molecule. In particular embodiments, the nucleic acid sequencing may be base extension sequencing. In some embodiments the nucleic acid sequencing may be chosen from ligase-based sequencing, or terminal-phosphate-labeled nucleotide sequencing.

By using nucleotide "bits," up to $4^n$ distinct capture molecules may be affixed and identified on a detecting system consistent with the present invention, where n is natural number representing the length of the ID sequenced. For example, 5 nucleotides could provide over a thousand unique IDs, while 12 nucleotides provide over 16 million combinations. For example, linker molecules may be affixed to a system consistent with the present invention and their locations may be determined by detecting their corresponding ID tag. The linker molecules then may serve as probes to, e.g., investigate binding interactions with one or more labeled sample molecules. That is, a system with one or more linker molecules affixed to it may serve as a probe array.

In certain embodiments, the labeled sample molecules may be fluorescently labeled. When bound to the capture molecule of a linker molecule, a labeled sample molecule may be detected by the light detector corresponding to the linker site where the linker molecule is affixed. Accordingly, in some embodiments, methods consistent with the present invention may further comprise the steps of applying a labeled sample molecule to a system consistent with the present invention and detecting the labeled sample molecule. In particular embodiments, the system may have linker molecules comprising a nucleic acid tag (ID) affixed to its linker sites. Multiple labeled sample molecules may be applied to a probe array simultaneously and be differentiated by their labels, e.g., by the intensity and/or wavelength of their fluorescent labels. Dissociation constants for binding interactions between sample molecules and labeled query molecules may be inferred based on both kinetics (e.g., rates of docking/undocking) and statistics (e.g., the portions of sample molecules in the bound or unbound state at any given time) at a given concentration of a labeled query molecule.

In some embodiments, the ID of a linking molecule may be at least 5, 10, 15, 20, 25, 30, 40, 50, 75, 90, 100, 150, 200, or more, nucleotides long. In some embodiments, the ID may be from 5 to 10, 20, 40, 80, or 160; or from 10 to 20 or 50; or from 20 to 35 nucleotides long. The ID contains a unique nucleic acid sequence, i.e., a nucleic acid to be detected. In particular embodiments, the unique nucleic acid sequence may be at least 1, 2, 4, 6, 8, 10, 12, 14, 16, 20, 24, 30, or more nucleotides long. In some embodiments, the unique nucleic acid sequence may be from 4 to 10, 12, 15, or 20; or from 10 to 20 nucleotides long. The ID may comprise at least one end link primer, i.e., the ID may contain a sequence complementary to a sequencing primer, which, in some embodiments, may be modified to attach to a linker site, e.g., by containing a biotinylated nucleotide. In some embodiments, the end link primer portion of the ID may be 3' to the unique nucleic acid sequence. In some embodiments, it may be 5' to the unique nucleic acid sequence. In still other embodiments, end link primers may be present at both the 3' and 5' ends of the unique nucleic acid sequence.

In certain embodiments, sample molecules and capture molecules may comprise moieties chosen from a carbohydrate, lipid, protein, peptide, antigen, nucleic acid, hormone, small organic molecule (e.g., a pharmaceutical), or vitamin moiety; or a combination thereof. These moieties may be naturally-occurring (e.g., biochemically purified) or synthetic (e.g., chemically synthesized or recombinantly produced). Additionally, these substrates may contain no, some, or all non-native components (e.g. non-natural amino acids, blocking or protecting groups, etc.). In particular embodiments, a sample molecule or capture molecules may be proteins, e.g., a growth factor, peptide antigen, antibody, or receptor.

Various means for conjugating nucleic acids to linker molecules or linker sites are known in the art, as reviewed in, e.g., U.S. Patent Publication No. 2004/0038331. The '331 publication discloses methods of forming protein oligonucleotide conjugates on a solid-phase support. U.S. Pat. No. 4,748,111 provides one example of conjugating a protein to the 3' end of a nucleic acid. There, terminal transferase is first used to add a ribose residue to the 3' portion of the molecule. A periodate oxidation reaction then generates a 3' aldehyde group on the nucleic acid, which then forms a covalent bond with an amide group of a protein. When a protein is conjugated to the 3' end of the ID, attachment to a linker site is via the 5' end of the ID.

In some embodiments, a capture molecule, e.g., a protein, may be linked to the 5' end of an ID. In these embodiments, the 3' end of the ID or 5' end of a sequencing primer may be used to affix capture molecule to a linker site. U.S. Pat. No. 6,013,434, for example, discloses oligonucleotide-polyamide conjugates, where the connection is via the 5' end of the oligonucleotide. U.S. Pat. No. 6,197,513 discloses both PNA and DNA conjugates to molecules with carboxylic acid moieties, e.g., proteins, via the 5' end of the nucleic acid. The PNA and DNA molecules contain arylamine or aminooxyacetyl moieties. U.S. Pat. No. 6,153,737 discloses oligonucleotides containing at least one 2' functionalized nucleoside, suitable for conjugating a variety of molecules to it.

3.1.3.4 Additional Detection Methods (a) FRET

In some embodiments, a molecule may be detected on a detecting apparatus provided by the invention by Förster resonance energy transfer (FRET), sometimes known as fluorescence resonance energy transfer. As is known in the art, FRET occurs when an excited donor molecule non-radiatively transfers energy to an acceptor molecule, which emits the energy, typically as light. FRET can help reduce background light by, e.g., providing greater spectral separation between effective excitation and emission wavelengths for a molecule being detected. FRET is often used to detect close molecular interactions since its efficiency decays as the sixth power of the distance between donor and acceptor molecules. For example, Zhang et al. (*Nature Materials* 4:826-31 (2005)) detected nucleic acid hybridization by FRET. There, a biotinylated nucleic acid target was conjugated to an avidin-coated quantum dot donor, which then excited a Cy5-conjugated DNA probe. In some embodiments, a labeled capture molecule and labeled sample molecule may form a donor/acceptor (or vice versa) pair for detection by FRET.

In some embodiments of nucleic acid sequencing provided by the invention, fluorescently labeled nucleotides may act as acceptor chromophores for a donor chromophore attached to a polymerase or ligase. Accordingly, in these embodiments, the donor chromophore located on the polymerase or ligase may excite an acceptor chromophore on a nucleotide being polymerized on, or ligated to, the sample nucleic acid. Nucleotides not proximate to the polymerase may be not excited due to the rapid falloff in FRET efficiency. In some embodiments the donor molecule may be, e.g., another fluorophore, e.g., a quantum dot. Quantum dots, e.g., semiconductor quantum dots are known in the art and are described in, e.g., International Publication No. WO 03/003015. Means of coupling quantum dots to, e.g., biomolecules are known in the art, as reviewed in, e.g., Medintz et al., *Nature Materials* 4:435-46 (2005) and U.S. Patent Publication Nos. 2006/0068506 and 2008/0087843, published Mar. 30, 2006 and Apr. 17, 2008, respectively. In some embodiments, quantum dots may be conjugated to a DNA polymerase molecule. As already discussed above for conjugating enzymes to linker sites, the skilled artisan will undoubtedly appreciate that when conjugating fluorophores to, e.g., a DNA polymerase or ligase, care must be taken to retain enzyme function by mitigating any effect of conjugating the fluorophore on the primary, secondary, and tertiary structures of the enzyme.

(b) Multi Photon Excitation

In some embodiments, a chromophore may be excited by two or more photons. For example, in some embodiments, excitation of either a donor or acceptor chromophore in FRET may be via two or more photons. Two photon and multi-photon excitation are described further in, e.g., U.S. Pat. Nos. 6,344,653 and 5,034,613.

(c) Time Resolved Detection

In some embodiments, the excitation light source and light detectors of an apparatus provided by the invention may be modulated to have a characteristic phase shift. Using methods known in the art, for example, as disclosed in U.S. Patent Publication No. 2008/0037008, published Feb. 14, 2008, light emitted from a molecule being detected on an apparatus provided by the invention may be measured by a corresponding light detector without interference from an excitation light source.

(d) Flow Cytometry

In some embodiments, the excitation light source and light detectors of an apparatus provided by the invention may be used to acquire flow cytometry data. Flow cytometry generally involves optical analysis of a population of objects in a liquid suspension. The suspension can be flowed past a detector, thereby allowing sequential detection of light from many objects in the population. The objects can be chosen from, for example, cells, microbeads, or other particles of similar sizes, such as particles greater than 0.1 µm, 0.2 µm, 0.5 µm, 1 µm, 2 µm, or 5 µm in at least one dimension (length, width, height, diameter, or the like, as appropriate for the shape of the particle), and/or smaller than 5 mm, 2 mm, 1 mm, 500 µm, 200 µm, 100 µm, 50 µm, 20 µm, or 10 µm in at least one dimension or all dimensions. The objects can be passed single-file between one or more excitation light sources and detectors, and fluorescence and/or light scattering data can be acquired. In some embodiments, the objects can comprise at least one, at least two, at least three, or at least four species of fluorophore. In some embodiments, light emitted by at least a subpopulation of the objects is detected.

The fluorophore can be chosen from, for example, fluorophores endogenously expressed by cells, such as fluorescent proteins (GFP, BFP, CFP, YFP, RFP, etc.), in addition to the fluorophores discussed above, including fluorophores with specific binding activity for a class of biomolecule or a cellular structure (e.g., DAPI, which is specific for DNA, or Evans Blue, which stains plasma membranes), fluorophores conjugated to nucleotide analogs, e.g., cyanine-dye conjugated dUTP, and synthetic fluorophores conjugated to a specific binding partner, such as an antibody, avidin, or a nucleic acid probe. The amount of fluorophore present in and/or bound to a particle, and therefore the amount of emission the fluorophore generates when excited by light of an appropriate wavelength, can be correlated to the presence and/or amount of a biomolecule, such as DNA, plasma membrane, or a specific nucleic acid, protein, other biomolecule, or metabolite in or on the particle.

Flow cytometry can comprise analyzing a population of particles to produce a frequency distribution of fluorescence intensities, such as a histogram. When more than one fluorophore is used and/or light scattering data is also acquired, or the data acquisition is time-resolved, the frequency distribution can be multidimensional. Use of a excitation light source and light detectors of an apparatus provided by the invention may result in high quality data, for example, by allowing data acquisition with high sensitivity and/or a high signal to noise ratio.

In some embodiments, methods of the invention comprising performing flow cytometry can further comprise fluorescence activated sorting. In such embodiments, particles are analyzed in real time by flow cytometry and sorted according to user-defined parameters. For example, particles exhibiting detectable fluorescence from a given fluorophore, or that exhibit such fluorescence within a given range, can be sorted apart from particles that do not meet the criterion. These particles can be collected for further analysis. In some embodiments, the particles sorted in this way are living cells. The sensitivity of detection apparatuses according to the invention may allow the sorting of cells with a low level of an activity, such as an enzyme activity or a promoter activity, apart from cells with undetectable activity and from cells with high activity. Thus, the methods and apparatuses of the invention may allow access to previously inaccessible enriched populations of cells with a given low promoter or enzyme activity.

(e) Other Fluorescent Detection Apparatuses and Methods

In some embodiments, methods of the invention relate to detection of light emitted by at least one object comprised by a biological cell, which can be a living or fixed cell. In some embodiments, the at least one object is chosen from at least one object comprising at least one quantum dot, at least one object comprising at least one fluorescent protein, and at least one object comprising at least one fluorescent small chemical moiety. In some embodiments, the at least one object is fluorescently labeled and comprises at least one oligonucleotide, polynucleotide, oligopeptide, polypeptide, oligosaccharide, polysaccharide, or lipid.

In some embodiments, the at least one object comprises a fixed and limited number of fluorophores, such as at most 20, 10, 5, or 2 fluorophores, which can be chosen from quantum dots, fluorescent proteins, and fluorescent small chemical moieties. In some embodiments, the at least one object comprises only a single fluorophore chosen from a quantum dot, a fluorescent protein, and a fluorescent small chemical moiety. Many examples of fluorescent small chemical moieties were discussed above. In some embodiments, fluorescent small chemical moieties may have an emission peak between 300 and 800 nm and/or a quantum yield (fraction of photons emitted per photon of peak absorption wavelength absorbed) of at least 0.1, 0.2, 0.3, 0.4, 0.5, 0.6, 0.7, 0.8, or 0.9.

3.2 Biomolecule Analysis Service

The present invention also provides a method of providing biomolecule analysis service using a detecting apparatus in accordance with embodiments consistent with the present invention. In some embodiments, the method may include the steps of providing a sample including a biomolecule to be analyzed from a service requester to a service provider and the service requester receiving analytical results from the service provider, wherein the results may be produced using an apparatus provided by the invention. In some embodiments, the method may be performed for remunerative consideration, e.g., fee-for-service or contract service agreements. In addition, the sample may be shipped directly between the service requester and the service provider, or mediated by a vendor. In some embodiments, the service provider or vendor may be geographically located in a territory outside of the United States of America, e.g. in another country.

4. EXAMPLES

Example I

Figure 17:
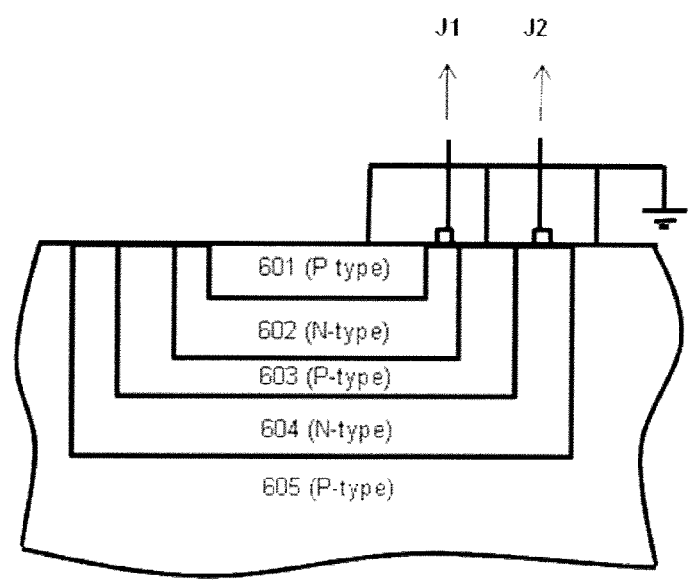
FIG. 17 is a view showing a multi-junction photodiode as an example of the light detector consistent with the present invention.

In this example, an apparatus as shown in FIG. 1 is used to detect and discriminate three types of objects. The light detector used in this example is a multi-junction photodiode with a P—N—P—N—P structure as shown in FIG. 17. P-type layer 601 and n-type layer 602 constitute the first optical sensor. P-type layer 603 and n-type layer 604 constitute the second optical sensor. All three p-type layers are connected to ground. The n-type layers 602 and 604 are connected to electrodes for outputting signals J1 and J2, respectively.

Figure 18:
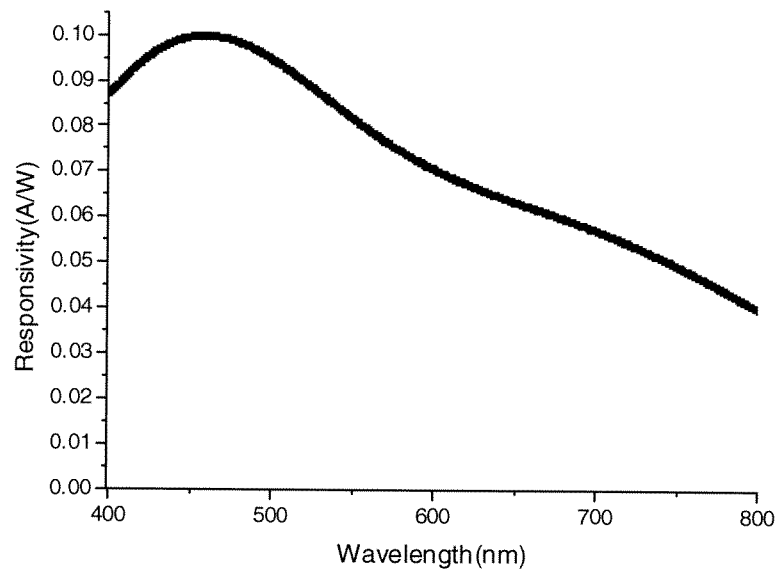
FIG. 18 is a graph showing the responsivity curve of one photodiode in the multi-junction photodiode of FIG. 11.
Figure 19:
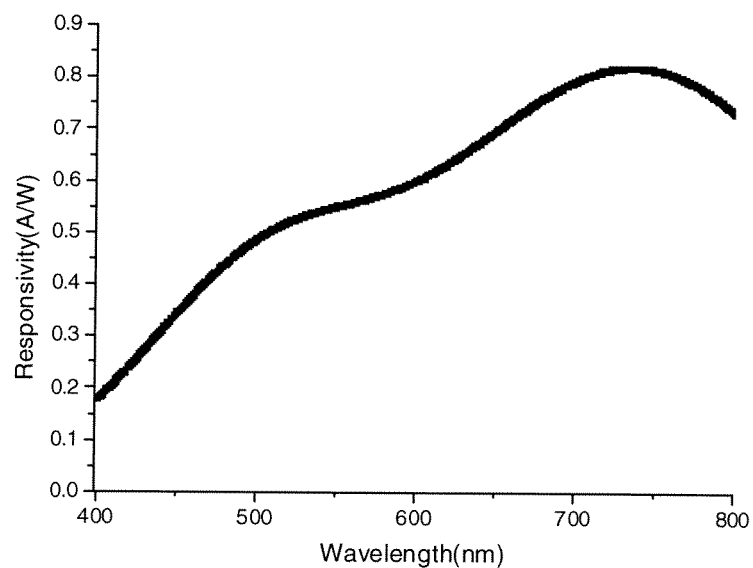
FIG. 19 is a graph showing the responsivity curve of another photodiode in the multi-junction photodiode of FIG. 11.

A 6.5 mW laser diode with a center wavelength of 407 nm is used as the excitation source to excite the object being detected. Light emitted from the object is incident on the light detector and is partially absorbed by the first optical sensor and the second optical sensor, sequentially. FIGS. 18 and 19 show the responsivity curves of the first optical sensor and the second optical sensor, respectively.

The multi-junction photodiode is enclosed inside a black box to minimize the impact of light from environment. A small hole is opened on the surface of the box above the photodiode. The object being detected is inserted through the hole to a detection zone, where the object is exposed to the excitation light emitted from the excitation source. A long-pass interference thin-film optical filter may be placed between the detection zone and the photodiode to partially block the scattered excitation light.

Figure 20:
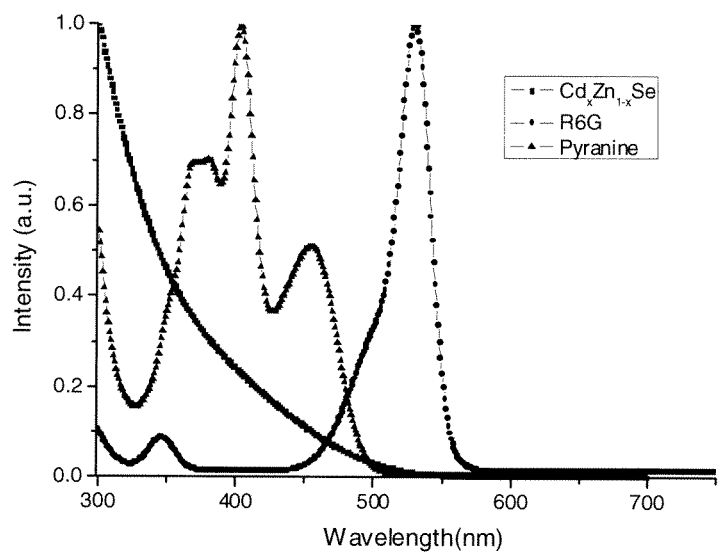
FIG. 20 is a graph showing the absorption spectra of three objects tested in one example of the present invention.
Figure 21:
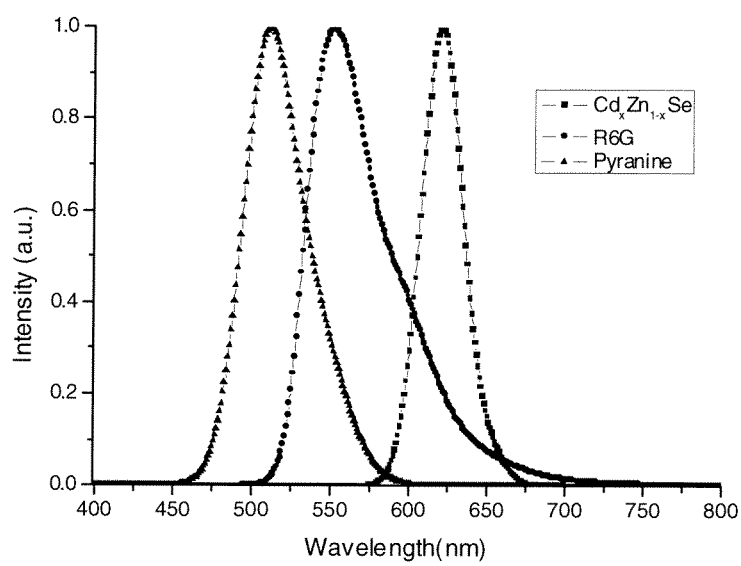
FIG. 21 is a graph showing the emission spectra of three objects tested in one example of the present invention.

Three objects are used to test the detecting apparatus. Object 1 is a first dye solution comprising Pyranine dissolved in deionized $H_2O$ with a concentration of $5.0 \times 10^{-5}$M, Object 2 is a second dye solution comprising Rhodamine 6G (R6G) dissolved in deionized $H_2O$ with a concentration of $5.0 \times 10^{-5}$M, and Object 3 is a quantum-dot solution comprising quantum dots with the composition of $Cd_xZn_{1-x}Se$ dissolved in Toluene with a concentration of $6.25 \times 10^{-4}$M FIGS. 20 and 21 show the absorption spectra and emission spectra of the three objects, respectively.

In this example, a reference sample comprising water without dye or quantum dot is also tested. The objects and the reference sample are tested one at each time. The output signal J1 from the first optical sensor and the output signal J2 from the second optical sensor and are recorded every 5.12 milli-second. A record of 10 consequent readings from each object and those from the reference sample is shown in Table 1.

TABLE 1

| | Output signals from the light detector | | | | | | | |
|---|---|---|---|---|---|---|---|---|
| Object | No object | | Object 1 | | Object 2 | | Object 3 | |
| Signal | J1 | J2 | J1 | J2 | J1 | J2 | J1 | J2 |
| 1 | 0.0012 | 0.017 | 0.4861 | 1.036 | 0.1423 | 0.787 | 0.051 | 0.3807 |
| 2 | 0.0022 | 0.017 | 0.4866 | 1.036 | 0.1428 | 0.787 | 0.0515 | 0.3807 |
| 3 | 0.0017 | 0.017 | 0.4851 | 1.036 | 0.1433 | 0.7865 | 0.051 | 0.3802 |
| 4 | 0.0017 | 0.017 | 0.4846 | 1.036 | 0.1418 | 0.7865 | 0.0505 | 0.3798 |
| 5 | 0.0007 | 0.0165 | 0.4866 | 1.036 | 0.1433 | 0.7865 | 0.0505 | 0.3807 |
| 6 | 0.0012 | 0.0165 | 0.4861 | 1.036 | 0.1423 | 0.787 | 0.0505 | 0.3807 |
| 7 | 0.0022 | 0.016 | 0.4851 | 1.036 | 0.1423 | 0.787 | 0.0501 | 0.3798 |
| 8 | 0.0022 | 0.016 | 0.4856 | 1.036 | 0.1428 | 0.787 | 0.0505 | 0.3812 |
| 9 | 0.0027 | 0.0165 | 0.4856 | 1.036 | 0.1438 | 0.7875 | 0.0501 | 0.3802 |
| 10 | 0.0022 | 0.0165 | 0.4851 | 1.036 | 0.1423 | 0.787 | 0.051 | 0.3798 |
| Average | 0.0020 | 0.017 | 0.486 | 1.036 | 0.143 | 0.787 | 0.051 | 0.380 |
| STD | 0.0006 | 0.0004 | 0.0007 | 0.0000 | 0.0006 | 0.0003 | 0.0004 | 0.0005 |

In this example, a value of 0.2 is selected as the threshold value for determining whether an object is present. If any one of the output signals J1 and J2 is higher than 0.2, it is determined that an object is present.

After the presence of an object is determined, a ratio R=J2/(2×J1) is calculated. If 0.5<R<1.5, it is determined that the object being detected is Object 1. If 2.0<R<3.0, it is determined that the object being detected is Object 2. If 3.5<R<4.5, it is determined that the object being detected is Object 3. Table 2 shows some examples of detecting results.

Detection of the Targets

The hybridized cDNA sample is transported to an electrode-embedded microfluidic reactor (Wang, T H et al., 2005) where a laser-focused detection region for single-molecule tracing is implemented. The sample solution is introduced at the inlet of a microchannel and then driven through by hydrodynamic pumping. When molecules enter the electrode region, their transport is governed by electrode-controlled electrokinetic forces, which steer them toward the region of minimal energy, located at the center of the middle

TABLE 2

Examples of detecting results

| Test Conditions | | | Operation and Result | | | | |
|---|---|---|---|---|---|---|---|
| | | | Presence | Criteria | Discrimination | | |
| | | | | | Object 1 | Object 2 | Object 3 |
| Reading | J1 | J2 | Type | If J1 or J2 > 0.2 | R = J2/(2 × J1) | 0.5 < R < 1.5 | 2.0 < R < 3.0 | 3.5 < R < 4.5 |
| 1 | 0.0017 | 0.0155 | No object | FALSE | — | — | — | — |
| 2 | 0.0032 | 0.0155 | No object | FALSE | — | — | — | — |
| 3 | 0.4856 | 1.036 | Object 1 | TRUE | 1.067 | TRUE | FALSE | FALSE |
| 4 | 0.4841 | 1.036 | Object 1 | TRUE | 1.070 | TRUE | FALSE | FALSE |
| 5 | 0.4851 | 1.036 | Object 1 | TRUE | 1.068 | TRUE | FALSE | FALSE |
| 6 | 0.1423 | 0.787 | Object 2 | TRUE | 2.765 | FALSE | TRUE | FALSE |
| 7 | 0.1423 | 0.7855 | Object 2 | TRUE | 2.760 | FALSE | TRUE | FALSE |
| 8 | 0.0501 | 0.3749 | Object 3 | TRUE | 3.742 | FALSE | FALSE | TRUE |
| 9 | 0.0476 | 0.3734 | Object 3 | TRUE | 3.922 | FALSE | FALSE | TRUE |
| 10 | 0.0501 | 0.3739 | Object 3 | TRUE | 3.732 | FALSE | FALSE | TRUE |

Example II

Recent study showed that a defect in cytokine activation may occur in HCV/HIV co-infected persons that limit efficient clearance of HCV from the liver. (J. Med. Virol. 78:202-207, 2006). HCV and HIV viral RNA of HCV mono-infected and HCV/HIV co-infected persons could be quantified using a molecular beacon approach and detector of Example 1.

RNA Extraction

Total RNA can be extracted from liver biopsies of HCV monoinfected and HCV/HIV co-infected persons using the High Pure RNA Tissue kit (Roche Diagnostics; Meylan, France) and elute in 100 ul of RNase-free water.

cDNA Synthesis

The extracted total RNA of liver biopsies is reverse transcribed with the Thermoscript Reverse Transcriptase kit using RC21 primer (5'-CTC CCG GGG CAC TCG CAA GC-3' (SEQ ID NO:1)) for HCV and gagR primer (5'-TTTGGTCCTTGTCTTA TGTCCAGAATG-3' (SEQ ID NO:2)) for HIV, respectively. The presence of any HCV or/and HIV RNA in the sample will incur reverse transcription and produce complementary single strand cDNAs. The RNA is then removed from the sample.

Molecular Beacon Probes

Different colors of molecular beacons are synthesized for detection of HCV or HIV. HCV: (5'-FAM-GCTAG-CATTTGGGCGTGCCCCCGCIAGAGCTAGC-DAB-CYL-3' (SEQ ID NO:3)). HIV: (5'-HEX-GCTAG-CATTTGGGCGTGCCCCCGCIAGAGCTAGC-DABCYL-3' (SEQ ID NO:4)). Detection of cDNA products in solution is carried out using Molecular Beacons (MBs) probes which was hybridized with their complementary sequences with denaturation step at 95° C. for 10 min, followed by annealing at 55° C. for 4 hours.

electrode. The focused laser beam of a confocal fluorescence spectroscope is positioned at the downstream end of the energy minimum region, wherein fluorescent bursts emitted from individual molecules are detected with a detector of Example 1. The presence of HCV and HIV in the sample are detected and discriminated from the dye labeled on the beacon probes using a method as in Example I. The amount of HCV and HIV viral RNA in the sample is quantified according to the number of the detection reported by the detecting apparatus.

For all patents, applications, or other reference cited herein, it should be understood that it is incorporated by reference in its entirety for all purposes as well as for the proposition that is recited. Where any conflict exits between a document incorporated by reference and the present application, this application will dominate.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A system for detecting an object capable of emitting light comprising: a nucleic acid object
a light detector for performing detection on the nucleic acid object, the light detector comprising a multi-junction photodiode which includes:
a first optical sensor including a first p-n junction and configured to generate a first output signal in response to the light; and
a second optical sensor including a second p-n junction and configured to generate a second output signal in response to the light,
wherein the first optical sensor is made of a first semiconductor material and the second optical sensor is made of a second semiconductor material different from the first semiconductor material, and the first and second optical sensors have different responsive properties; and
a computer configured to:
sum the first and second output signals to obtain a total signal,
divide the second output signal by the total signal to obtain a first ratio, compare the first ratio to a first range corresponding to a known type,
divide the first output signal by the second output signal to obtain a second ratio, and
confirm whether the object belongs to the known type by determining whether the second ratio is within a second range corresponding to the known type,
wherein the object is a nucleic acid.

2. The apparatus of claim 1, further comprising:
an optical structure collecting and directing a light emitted from the object to the optical sensors.

3. The apparatus of claim 2, wherein the optical structure comprises a prism.

4. The apparatus of claim 2, wherein the optical structure comprises a grating.

5. The apparatus of claim 2, wherein the optical structure comprises a lens.

6. The apparatus of claim 2, wherein the optical structure comprises an optical filter.

7. The apparatus of claim 1, wherein the at least two optical sensors are stacked.

8. The apparatus of claim 1, wherein the at least two optical sensors are arranged horizontally.

9. The apparatus of claim 1, wherein the optical sensors are photodiodes.

10. The apparatus of claim 7, wherein the at least two optical sensors are formed by at least two stacking p-n junctions within one device.

11. The apparatus of claim 1, wherein the light detector comprises a circuit of signal amplifier, A/D convertor, integrator, comparator, logic circuit, readout circuit, memory, microprocessor, clock, and/or address.

12. The apparatus of claim 1, wherein the object comprises at least one quantum dot, at least one fluorescent protein, or at least one fluorescent small chemical moiety.

13. The apparatus of claim 1, wherein the object is fluorescently labeled and comprises at least one oligonucleotide, polynucleotide, oligopeptide, polypeptide, oligosaccharide, polysaccharide, or lipid.

14. The apparatus of claim 1, wherein the object is a single molecule.

15. The apparatus of claim 1, wherein the object comprises a target object without light emitting capability and a labeling object with light emitting capability.

16. The apparatus of claim 1, wherein the object comprises a target object without light emitting capability and a group of labeling objects with light emitting capability.

17. The apparatus of claim 1, wherein the object comprises only a single fluorophore chosen from a quantum dot, a fluorescent protein, and a fluorescent small chemical moiety.

18. The apparatus of claim 1, wherein the light detector is one of at least one light detector for detecting a plurality of objects, the plurality of objects are comprised by a liquid suspension, and the suspension flows past the at least one light detector.

19. A method for detecting an object capable of emitting light comprising: a nucleic acid object
providing a light detector for performing detection on the nucleic acid object, the light detector comprising a multi-junction photodiode which includes:
a first optical sensor including a first p-n junction and configured to generate a first output signal in response to the light; and
a second optical sensor including a second p-n junction and configured to generate a second output signal in response to the light,
wherein the first optical sensor is made of a first semiconductor material and the second optical sensor is made of a second semiconductor material different from the first semiconductor material, and the first and second optical sensors have different responsive properties;
summing the first and second output signals to obtain a total signal;
dividing the second output signal by the total signal to obtain a first ratio; compare the first ratio to a first range corresponding to a known type;
dividing the first output signal by the second output signal to obtain a second ratio; and
confirming whether the object belongs to the known type by determining whether the second ratio is within a second range corresponding to the known type,
wherein the object is a nucleic acid.

20. The method of claim 19, wherein the object comprises at least one quantum dot, at least one fluorescent protein, or at least one fluorescent small chemical moiety.

21. The method of claim 19, wherein the object is fluorescently labeled and comprises at least one oligonucleotide, polynucleotide, oligopeptide, polypeptide, oligosaccharide, polysaccharide, or lipid.

22. The method of claim 19, wherein the object is a single molecule.

23. The method of claim 19, wherein the object comprises a target object without light emitting capability and a labeling object with light emitting capability.

24. The method of claim 19, wherein the object comprises a target object without light emitting capability and a group of labeling objects with light emitting capability.

25. The method of claim 19, wherein the object comprises only a single fluorophore chosen from a quantum dot, a fluorescent protein, and a fluorescent small chemical moiety.

26. The method of claim 19, further comprising detecting a plurality of objects using at least one light detector, wherein the plurality of objects are comprised by a liquid suspension, and the method further comprises flowing the suspension past the at least one light detector.

27. The apparatus according to claim 1, further comprising a non-transitory computer-readable medium encoded with a computer program product, the computer program product, when executed by the computer, instructing the computer to perform the steps of:
   receiving a first output signal generated by a first optical sensor in response to light emitted by an object and a second output signal generated by a second optical sensor in response to the light, the first and second optical sensors being made of different semiconductor materials and having different responsive properties;
   summing the first and second output signals to obtain a total signal;
   determining whether the total signal is equal to or larger than a threshold value;
   if the total signal is equal to or larger than the threshold value, dividing the second output signal by the total signal to obtain a first ratio;
   determining whether the first ratio is within a first range corresponding to a known type;
   if the first ratio is within the first range, dividing the first output signal by the second output signal to obtain a second ratio; and
   confirming whether the object belongs to the known type by determining whether the second ratio is within a second range corresponding to the known type.

\* \* \* \* \*